US010610184B2

(12) United States Patent
Sakaguchi et al.

(10) Patent No.: US 10,610,184 B2
(45) Date of Patent: Apr. 7, 2020

(54) MEDICAL-INFORMATION PROCESSING APPARATUS AND X-RAY CT APPARATUS

(71) Applicant: Canon Medical Systems Corporation, Otawara-shi (JP)

(72) Inventors: Takuya Sakaguchi, Utsunomiya (JP); Kenji Hirohata, Minato-ku (JP)

(73) Assignee: Canon Medical Systems Corporation, Otawara-shi (JP)

( * ) Notice: Subject to any disclaimer, the term of this patent is extended or adjusted under 35 U.S.C. 154(b) by 17 days.

(21) Appl. No.: 15/673,858

(22) Filed: Aug. 10, 2017

(65) Prior Publication Data
US 2018/0042569 A1 Feb. 15, 2018

(30) Foreign Application Priority Data

Aug. 12, 2016 (JP) .................................. 2016-158737

(51) Int. Cl.
*A61B 6/00* (2006.01)
*A61B 6/03* (2006.01)
(Continued)

(52) U.S. Cl.
CPC ............ *A61B 6/5217* (2013.01); *A61B 6/032* (2013.01); *A61B 6/504* (2013.01); *A61B 6/507* (2013.01);
(Continued)

(58) Field of Classification Search
None
See application file for complete search history.

(56) References Cited

U.S. PATENT DOCUMENTS 7,775,988 B2* 8/2010 Pijls ..................... A61B 5/028
600/504
2004/0059220 A1* 3/2004 Mourad ............... A61B 5/0048
600/442
(Continued)

FOREIGN PATENT DOCUMENTS

JP 2014-100249 6/2014
JP 2014-113264 6/2014
(Continued)

OTHER PUBLICATIONS

Hirohata et al., "A novel CT-FFR method for the coronary artery based on 4DCT image analysis and structural and fluid analysis," Proc. SPIE 9412, Medical Imaging 2015: Physics of Medical Imaging, 94122O (Mar. 18, 2015); doi: 10.1117/12.2081674 (Year: 2015).*
(Continued)

*Primary Examiner* — Soo Shin
(74) *Attorney, Agent, or Firm* — Oblon, McClelland, Maier & Neustadt, L.L.P.

(57) ABSTRACT

A medical-information processing apparatus according to an embodiment includes processing circuitry. The processing circuitry acquires medical image data that is obtained during imaging on the subject in a resting state in the time phase where the relationship between the volume of blood flow and the pressure in a blood vessel in the cardiac cycle of the subject indicates a proportional relationship. The processing circuitry extracts the structure of a blood vessel, included in the medical image data, applies fluid analysis to the structure of the blood vessel to obtain a first index value, which is obtained based on the pressure in the blood vessel on the upstream side of a predetermined position within the blood vessel and the relation equation between the volume of blood flow and the pressure in the blood vessel in the resting state, and a second index value, which is obtained based on
(Continued)

the pressure in the blood vessel on the downstream side of the predetermined position and the relation equation, and calculates the pressure ratio, which is the ratio of the first index value to the second index value.

39 Claims, 9 Drawing Sheets

(51) Int. Cl.
*G06T 11/20* (2006.01)
*G06T 7/00* (2017.01)

(52) U.S. Cl.
CPC .......... *A61B 6/5229* (2013.01); *A61B 6/5247* (2013.01); *A61B 6/541* (2013.01); *A61B 6/545* (2013.01); *G06T 7/0016* (2013.01); *A61B 6/461* (2013.01); *A61B 6/463* (2013.01); *A61B 6/469* (2013.01); *A61B 6/503* (2013.01); *A61B 6/5294* (2013.01); *A61B 2576/023* (2013.01); *G06T 11/206* (2013.01); *G06T 2207/10081* (2013.01); *G06T 2207/30048* (2013.01); *G06T 2207/30104* (2013.01)

(56) References Cited

U.S. PATENT DOCUMENTS

| | | | | |
|---|---|---|---|---|
| 2013/0226003 A1* | 8/2013 | Edic | ............................ | G06T 7/30 600/454 |
| 2014/0100451 A1* | 4/2014 | Tolkowsky | ............ | A61B 6/507 600/424 |
| 2014/0107479 A1 | 4/2014 | Klaiman et al. | | |
| 2014/0114184 A1 | 4/2014 | Klaiman et al. | | |
| 2014/0114185 A1 | 4/2014 | Tolkowsky et al. | | |
| 2014/0187920 A1 | 7/2014 | Millett et al. | | |
| 2015/0245776 A1* | 9/2015 | Hirohata | ................. | A61B 6/032 600/504 |
| 2015/0313478 A1* | 11/2015 | Veszelei | ............... | A61B 5/0215 600/483 |
| 2015/0356734 A1 | 12/2015 | Ooga et al. | | |

FOREIGN PATENT DOCUMENTS

| | | |
|---|---|---|
| JP | 2015-097724 | 5/2015 |
| JP | 2015-527901 | 9/2015 |
| JP | 2016-507280 | 3/2016 |

OTHER PUBLICATIONS

Nico H.J. Pijls, et al., "Experimental Basis of Determining Maximum Coronary, Myocardial, and Collateral Blood Flow by Pressure Measurements for Assessing Functional Stenosis Severity Before and After Percutaneous Transluminal Coronary Angioplasty," 1993, Circulation 87; 15 pages.

Nico H.J. Pijls, et al., "Percutaneous Coronary Intervention of Functionally Nonsignificant Stenosis: 5-Year Follow-Up of the DEFER Study," 2007, vol. 49, No. 21, pp. 2105-2111.

James K. Min. et al., "Rationale and Design of the DeFACTO (Determination of Fractional Flow Reserve by Anatomic Computed Tomographic Angiography) Study," Journal of Cardiovascular Computed Tomography, 2011, pp. 301-309.

Ronald F. Bellamy, "Diastolic Coronary Artery Pressure-Flow Relations in the Dog," Circulation Research, Jul. 1978, vol. 43 No. 1, 11 pages.

K. Hirohata, et al., "A Novel CT-FFR method for the coronary artery based on 4D-CT image analysis and structural and fluid analysis," 2015, Proc. of SPIE vol. 9412, pp. 1-15.

Mitsuaki Kato, et al., "Fast CT-FFR Analysis Method for the Coronary Artery Based on 4D-CT Image Analysis and Structural and Fluid Anaiysis", 2015, Proc. of ASME, pp. 1-10.

Sayan Sen, et al., "Development and Validation of a New Adenosine-Independent Index of Stenosis Severity From Coronary Wave-Intensity Analysis: Results of the ADVISE (ADonosine Vasodilator Independent Stenosis Evaluation) Study", 2012, Journal of the American College of Cardiology vol. 59 No. 15, pp. 1392-1402.

\* cited by examiner

MEDICAL-INFORMATION PROCESSING APPARATUS AND X-RAY CT APPARATUS

CROSS-REFERENCE TO RELATED APPLICATIONS

This application is based upon and claims the benefit of priority from Japanese Patent Application No. 2016-158737, filed on Aug. 12, 2016; the entire contents of which are incorporated herein by reference.

FIELD

Embodiments described herein relate generally to a medical-information processing apparatus and an X-ray CT apparatus.

BACKGROUND

It is conventionally known that the causes of ischemic disorders of organs are broadly divided into poor blood circulation and functional impairment of organs themselves. For example, stenosis, which is an example of poor blood circulation of the coronary artery, is a significant lesion that causes ischemic heart diseases, and there is a need to determine whether drug treatment is to be conducted, whether stent treatment is to be conducted, or the like, for the ischemic heart diseases. In recent years, for diagnosis that conducts evaluation of hematogenous ischemia in the coronary artery, there has been a suggested technique for measuring Fractional Flow Reserve (FFR) by using a pressure wire during coronary artery contrast examination (coronary angiography: CAG) using a catheter.

The FFR is the index for assuming how much blood flow is disturbed by a lesion, such as stenosis, and it is defined by using the ratio of the flow volume in a case where there is no lesion to the flow volume in a case where there is a lesion. Here, during the actual FFR measurement, the measurement is conducted by replacing the flow volume within a blood vessel with the pressure. For example, during the FFR measurement, adenosine is administered to obtain the maximum engorged state (blood-vessel expanded state) so that the relationship between the flow volume and the pressure within a blood vessel is a proportional relationship, and the flow volume that defines the FFR is replaced with the pressure. Thus, the FFR may be measured on the basis of the pressure within a blood vessel, measured by using the above-described pressure wire.

Furthermore, in recent years, there has been a known technique for conducting FFR measurement without administering the above-described adenosine. According to the above-described technique that uses adenosine, adenosine is administered so that the relationship between the flow volume and the pressure within s blood vessel becomes a proportional relationship and the pressure within the blood vessel is measured; however, in the case of the technique that is conducted without administering adenosine, the pressure is measured in the time phase where the relationship between the flow volume and the pressure within a blood vessel in a resting state is a proportional relationship. Specifically, as the relationship between the flow volume and the pressure within a blood vessel is a proportional relationship even in a resting state during the wave-free period (the period in which the vascular resistance is smaller and stable) in the cardiac cycle, the FFR is measured on the basis of the pressure that is measured by using a pressure wire during the wave-free period according to the technique that is conducted without administering adenosine.

As described above, the FFR measurement is conducted by using a pressure wire for diagnosis that conducts evaluation of hematogenous ischemia in the coronary artery; however, contrary to the above-described FFR measurement, that uses a pressure wire, in recent years, there has been a known technique for conducting evaluation of hematogenous ischemia in the coronary artery in a non-invasive manner by using medical images of the heart, collected by medical-image diagnostic apparatus, such as X-ray computed tomography (CT) apparatus, magnetic resonance imaging (MRI) apparatus, or ultrasonic diagnostic apparatus. Recently, hematogenous ischemia evaluation has been conducted by using the above-described various techniques, and treatments are given in according to the evaluation.

DETAILED DESCRIPTION

According to an embodiment, a medical-information processing apparatus includes processing circuitry. The processing circuitry is configured to acquire medical image data that is obtained during imaging on a subject in a resting state in a time phase where a relationship between a volume of blood flow and a pressure in a blood vessel in a cardiac cycle of the subject indicates a proportional relationship. The processing circuitry is configured to extract a structure of a blood vessel, included in the medical image data, applies fluid analysis to the structure of the blood vessel to obtain a first index value, which is obtained based on a pressure in the blood vessel on an upstream side of a predetermined position within the blood vessel and a relation equation between a volume of blood flow and a pressure in the blood vessel in the resting state, and a second index value, which is obtained based on a pressure in the blood vessel on a downstream side of the predetermined position and the relation equation. The processing circuitry is configured to calculate a pressure ratio, which is a ratio of the first index value to the second index value.

A detailed explanation is given below of an embodiment of a medical-information processing apparatus and an X-ray CT apparatus according to the subject application with reference to the attached drawings. Furthermore, the medical-information processing apparatus and the X-ray CT apparatus according to the subject application are not limited to the embodiments described below.

First Embodiment

First, a first embodiment is explained. In the first embodiment, an explanation is given of an example of the case where the technology according to the subject application is applied to a medical-information processing apparatus. Furthermore, a medical-information processing system that includes the medical-information processing apparatus is explained as an example below. Moreover, an explanation is given below of an example of the case where, for example, a blood vessel of the heart is the target for analysis.

Figure 1:
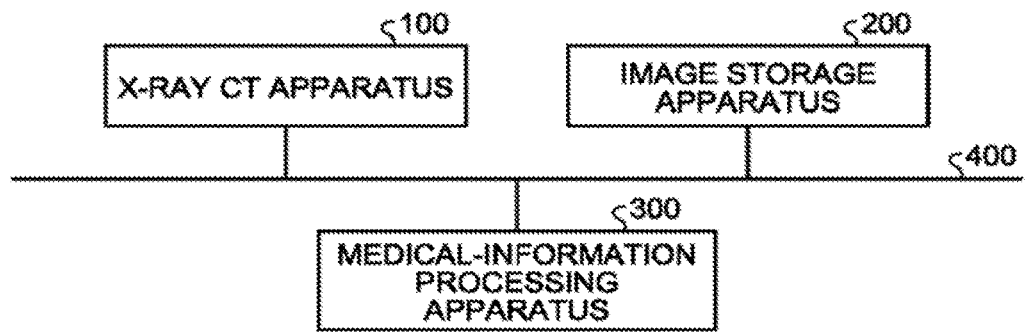
FIG. 1 is a diagram that illustrates an example of the configuration of a medical-information, processing system according to a first embodiment.

FIG. 1 is a diagram that illustrates an example of the configuration of the medical-information processing system according to the first embodiment. As illustrated in FIG. 1, the medical-information processing system according to the first embodiment includes an X-ray computed tomography (CT) apparatus 100, an image storage apparatus 200, and a medical-information processing apparatus 300.

As illustrated in FIG. 1, for example, the medical-information processing apparatus 300 according to the first embodiment is connected to the X-ray CT apparatus 100 and the image storage apparatus 200 via a network 400. Furthermore, the medical-information processing system may be further connected to different medical-image diagnostic apparatus, such as MRI apparatus, ultrasonic diagnostic apparatus, or positron emission tomography (PET) apparatus, via the network 400.

The X-ray CT apparatus 100 collects CT image data (volume data) on the subject. Specifically, the X-ray CT apparatus 100 moves and rotates an X-ray tube and an X-ray detector with the subject at substantially the center and detects X-rays, which are transmitted through the subject, to collect projection data. Then, the X-ray CT apparatus 100 generates three-dimensional CT image data in chronological order on the basis of the collected projection data.

The image storage apparatus 200 stores image data that is collected by various medical-image diagnostic apparatus. For example, the image storage apparatus 200 is implemented by a computer apparatus such as a server apparatus. According to the present embodiment, the image storage apparatus 200 acquires CT image data (volume data) from the X-ray CT apparatus 100 via the network 400 and stores the acquired CT image data in a memory that is provided inside or outside the apparatus.

The medical-information processing apparatus 300 acquires image data from various medical-image diagnostic apparatus via the network 400 and processes the acquired image data. For example, the medical-information processing apparatus 300 is implemented by a computer apparatus, such as workstation. According to the present embodiment, the medical-information processing apparatus 300 acquires CT image data from the X-ray CT apparatus 100 or the image storage apparatus 200 via the network 400 and conducts various types of image processing on the acquired CT image data. Then, the medical-information processing apparatus 300 presents CT image data, on which image processing has not been performed or it has been performed, on a display, or the like.

Figure 2:
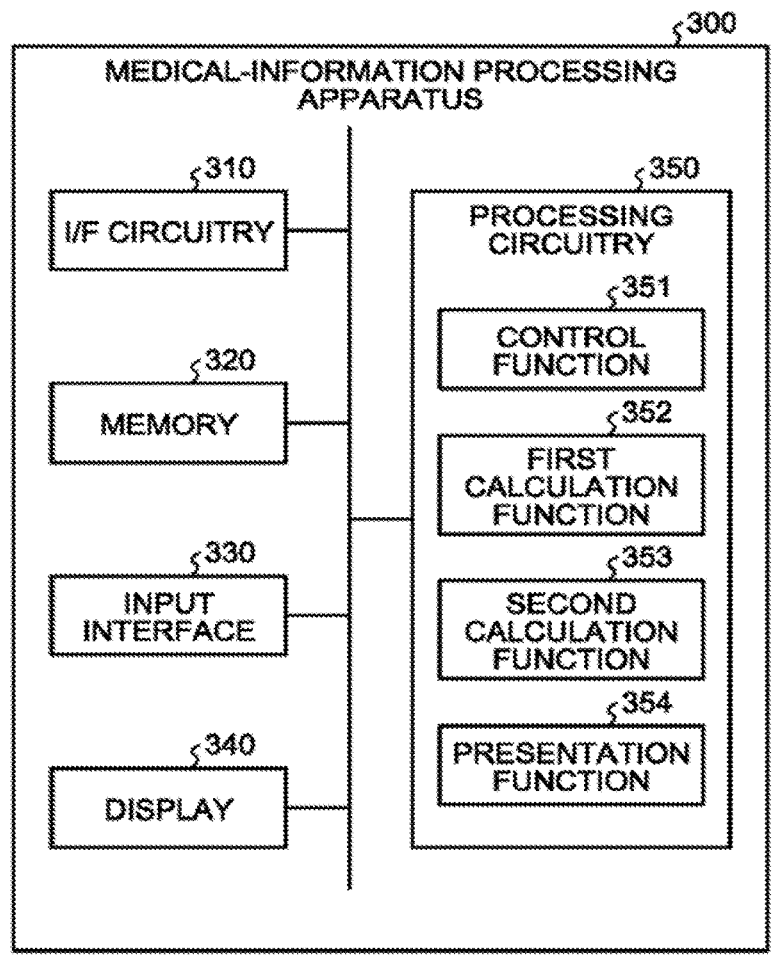
FIG. 2 is a diagram that illustrates an example of the configuration of the medical-information processing apparatus according to the first embodiment.

FIG. 2 is a diagram that illustrates an example of the configuration of the medical-information processing apparatus 300 according to the first embodiment. For example, as illustrated in FIG. 2, the medical-information processing apparatus 300 includes interface (I/F) circuitry 310, a memory 320, an input interface 330, a display 340, and processing circuitry 350.

The I/F circuitry 310 is connected to the processing circuitry 350, and it controls transmission of various types of data and communications that are conducted with various connected medical-image diagnostic apparatus or the image storage apparatus 200 via the network 400. For example, the I/F circuitry 310 is implemented by a network card, a network adapter, a Network Interface Controller (NIC), or the like. According to the present embodiment, the I/F circuitry 310 receives CT image data from the X-ray CT apparatus 100 or the image storage apparatus 200 and outputs the received CT image data to the processing circuitry 350.

The memory 320 is connected to the processing circuitry 350, and it stores various types of data. For example, the memory 320 is implemented by a semiconductor memory device, such as a random access memory (RAM) or a flash memory, a hard disk, an optical disk, or the like. According to the present embodiment, the memory 320 stores CT image data that is received from the X-ray CT apparatus 100 or the image storage apparatus 200.

The input interface 330 is connected to the processing circuitry 350, and it converts input operations, received from an operator, into electric signals and outputs them to the processing circuitry 350. For example, the input interface 330 is implemented by a trackball, a switch button, a mouse, a keyboard, a touch panel, or the like.

The display 340 is connected to the processing circuitry 350, and it presents various types of information and various types of image data, output from the processing circuitry 350. For example, the display 340 is implemented by a liquid crystal monitor, a cathode ray tube (CRT) monitor, a touch panel, or the like.

The processing circuitry 350 controls each component, included in the medical-information processing apparatus 300, in accordance with input operations that are received from an operator via the input interface 330. For example, the processing circuitry 350 is implemented by a processor. According to the present embodiment, the processing circuitry 350 causes the memory 320 to store CT image data that is output from the I/F circuitry 310. Furthermore, the processing circuitry 350 reads CT image data from the memory 320 and presents it on the display 340.

With this configuration, the medical-information processing apparatus 300 according to the present embodiment makes it possible to improve the accuracy of diagnosis with regard to blood flow. Specifically, for calculation of index values that are intended for the subject in a resting state, the medical-information processing apparatus 300 calculates more accurate index values, thereby improving the accuracy of diagnosis with regard to blood flow. Furthermore, for non-invasive calculation of index values that are intended for the subject in a resting state, the medical-information processing apparatus 300 calculates and presents more accurate index values and index values that correspond, to invasively measured index values, thereby improving the accuracy of diagnosis with regard to blood flow in a non-invasive manner. As described above, for hematogenous ischemia evaluation, in the case of invasive evaluation using a catheter, adenosine is administered to the subject, and the pressure is measured in the maximum engorged state so that the fractional flow reserve (FFR) is calculated. Alternatively, in the case of invasive evaluation using a catheter, adenosine is not administered, and the pressure is measured during the wave-free period in the cardiac cycle in a resting state so that the FFR is calculated (hereafter, the FFR, measured during the wave-free period in a resting state, is described as the instantaneous FFR).

The instantaneous FFR is an index value that has received attention in recent years because it may reduce loads on the subject as adenosine is not administered and it has the characteristics (e.g., it reflects an effect of the heart muscle, a measurement may be conducted even if there are multiple stenoses in a single blood vessel, or the like), which are not included in the FFR. Upon calculation of the above instantaneous FFR, the medical-information processing apparatus 300 according to the present embodiment calculates an index value that represents the proportional relationship between the flow volume and the pressure within a blood vessel with more accuracy. Furthermore, upon calculation of instantaneous FFR in a non-invasive manner, the medical-information processing apparatus 300 calculates an index value that represents the proportional relationship between the flow volume and the pressure within a blood vessel with more accuracy and an index value that corresponds to the instantaneous FFR that is invasively measured by using a catheter.

To perform the above-described process, as illustrated in FIG. 2, the processing circuitry 350 in the medical-information processing apparatus 300 according to the first embodiment executes a control function 351, a first calculation function 352, a second calculation function 353, and a presentation function 354. Here, the processing circuitry 350 is an example of the processing circuitry in claims.

The control function 351 performs the overall control on the medical-information processing apparatus 300. Furthermore, the control function 351 acquires the medical image data that is obtained when the subject in the resting state is captured in the time phase where the relationship between the volume of blood flow and the pressure in the blood vessel in the cardiac cycle of the subject indicates a proportional relationship. The first calculation function 352 performs a first calculation process to calculate the pressure on the upstream side of a predetermined position within a blood vessel, the pressure on the downstream side thereof, and the pressure at the time of zero flow volume due to fluid analysis that uses the image data that is collected in the time phase, in which the relationship between the volume of blood flow and the pressure in the blood vessel indicates a proportional relationship, in the cardiac cycle of the subject in the resting state. Furthermore, an explanation is given below of the process performed by the medical-information processing apparatus 300 by using an example of the case where the predetermined position is a lesion area, such as stenosis; however, embodiments are not limited thereto, and the target may be any position within a blood vessel.

For example, the first calculation function 352 calculates the pressure on the upstream side of a lesion area within a blood vessel, the pressure on the downstream side of the lesion area, and the pressure at the time of zero flow volume, which indicates the pressure in a case where the volume of blood flow within a blood vessel is zero, due to the fluid analysis that uses the image data that is collected in the time phase where the relationship between the volume of blood flow and the pressure in the blood vessel indicates a proportional relationship in the cardiac cycle of the subject in a resting state. Specifically, the first calculation function 352 executes fluid analysis by using the image data that contains a blood vessel (e.g., coronary artery) in the wave-free period of the subject, to which adenosine is not administered and which is in a resting state, and it calculates indexes related to the blood flow, including the pressure on the upstream side of the lesion area (for example, stenosis), the pressure on the downstream side, and the pressure at the time of zero flow volume.

Furthermore, examples of the index of the blood flow, calculated by the first calculation function 352, include a mechanical index within a blood vessel or an index related to the volume of blood flow. Examples of the mechanical index within a blood vessel include a pressure, a vector, or a shear stress. Moreover, the index related to the volume of blood flow includes the volume of flow, the flow velocity, or the like. The fluid analysis by the first calculation function 352 is explained below.

The first calculation function 352 executes fluid analysis on the basis of CT image data. Specifically, the first calculation function 352 extracts blood-vessel form data in chronological order, which indicates the form of a blood vessel, from three-dimensional CT image data. For example, the first calculation function 352 reads CT image data in multiple time phases, collected over time, from the memory 320 and performs image processing on the read CT image data in time phases, thereby extracting blood-vessel form data in chronological order.

Here, the first calculation function 352 sets the target area, for which an index value is calculated, in a blood vessel area that is included in CT image data. Specifically, the first calculation function 352 sets the target area in the blood vessel area in accordance with commands or image processing by an operator via the input interface 330. Then, as the blood-vessel form data on the set target area, the first calculation function 352 extracts, from CT image data, for example the central line of a blood vessel (coordinates information on the central line), the cross-sectional areas of a blood vessel and an inner cavity on the cross-section that is perpendicular to the central line, or the distance from the central line to the inner wall and the distance from the central line to the outer wall in a cylinder direction on the cross-section that is perpendicular to the central line. Furthermore, the first calculation function 352 may extract other various types of blood-vessel form data in accordance with an analysis technique.

Furthermore, the first calculation function 352 sets an analysis condition of the fluid analysis. Specifically, the first calculation function 352 sets a property value of blood, a condition of repeated calculation, a default, value of analysis, or the like, as an analysis condition. For example, the first calculation function 352 sets the viscosity or the density of blood, or the like, as the property value of blood. Furthermore, the first calculation function 352 sets the maximum number of times of repetition during repeated calculation, a relaxation coefficient, an acceptable value of residual error, or the like, as the condition of repeated calculation. Furthermore, the first calculation function 352 sets a flow volume, a pressure, a fluid resistance, a default value of pressure boundary, or the like, as the default value of analysis. Moreover, various values, used by the first calculation function 352, may be previously installed in a system, or it may be defined interactively by an operator.

Furthermore, the first calculation function 352 calculates the index related to the blood flow of a blood vessel due to fluid analysis that uses the image data that includes the blood vessel. Specifically, the first calculation function 352 executes a fluid analysis that uses blood-vessel form data and the analysis condition to calculate the index related to the blood flow in the target area of the blood vessel. For example, on the basis of the blood-vessel form data, such as the outline of the inner cavity or the outer wall of a blood vessel or the cross-sectional area, the central line, or the like, of a blood vessel, and the setting condition, such as the property value of blood, a condition of repeated calculation, or a default value of analysis, the first calculation function 352 calculates an index, such as pressure, blood flow volume, blood flow velocity, vector, or shear stress, for each predetermined position of a blood vessel. Furthermore, the first calculation function 352 uses time fluctuations in the blood-vessel form data, such as the outline of the inner cavity or the outer wall of a blood vessel or the cross-sectional area, the central line, or the like, of a blood vessel, to calculate time fluctuations in an index, such as pressure, blood flow volume, blood flow velocity, vector, or shear stress. Here, the first calculation function 352 searches for the pressure that makes the flow volume/the flow velocity zero, thereby estimating the pressure at the time of zero flow volume.

Figure 3:
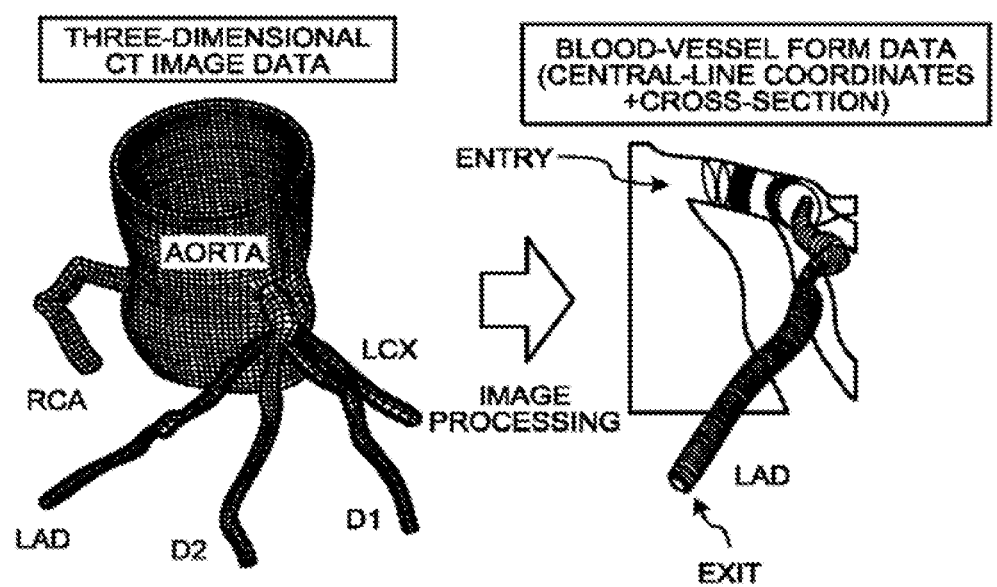
FIG. 3 is a diagram that illustrates an example of the process performed by a first calculation function according to the first embodiment.

FIG. 3 is a diagram that illustrates an example of the operation by the first calculation function 352 according to the first embodiment. As illustrated in FIG. 3, for example, the first calculation function 352 extracts the blood-vessel form data, which includes the coordinates of the central line or the cross-section information, with regard to the LAD, which is the target area, from the three-dimensional CT image data that includes the aorta and the coronary artery. Furthermore, the first calculation function 352 sets an analysis condition for the analysis that is intended for the extracted LAD. Then, the first calculation function 352 conducts fluid analysis by using the blood-vessel form data on the extracted LAD and the set condition so as to calculate an index, such as pressure, blood flow volume, blood flow velocity, vector, or shear stress, for each predetermined position along the central line from the entry boundary of the target area LAD to the exit boundary, for example. That is, the first calculation function 352 calculates the distribution of the pressure, the blood floor volume, the blood flow velocity, the vector, the shear stress, or the like, with regard to the target area and further calculates the pressure at the time of zero flow volume.

As described above, the first calculation function 352 extracts blood-vessel form data from each of sets of CT image data in time phases, collected over time, and conducts fluid analysis by using the extracted blood-vessel form data in time phases and the analysis condition, thereby calculating the index with regard to the blood flow. Here, the first calculation function 352 extracts blood-vessel form data by using CT image data in the wave-free period, where the relationship between the flow volume and the pressure within a blood vessel in the subject in a resting state is a proportional relationship. That is, the first calculation function 352 uses CT image data in the wave-free period, thereby making it possible to calculate the instantaneous FFR using the pressure where the relationship between the flow volume and the pressure is a proportional relationship and the subject in a resting state is targeted. Furthermore, if the relationship between the flow volume and the pressure in a blood vessel indicates a proportional relationship, it may be considered that the vascular resistance in the blood vessel is stable. That is, the time phase where the relationship between the flow volume and the pressure indicates a proportional relationship may be restated as the time phase where the vascular resistance is stable.

Figure 4:
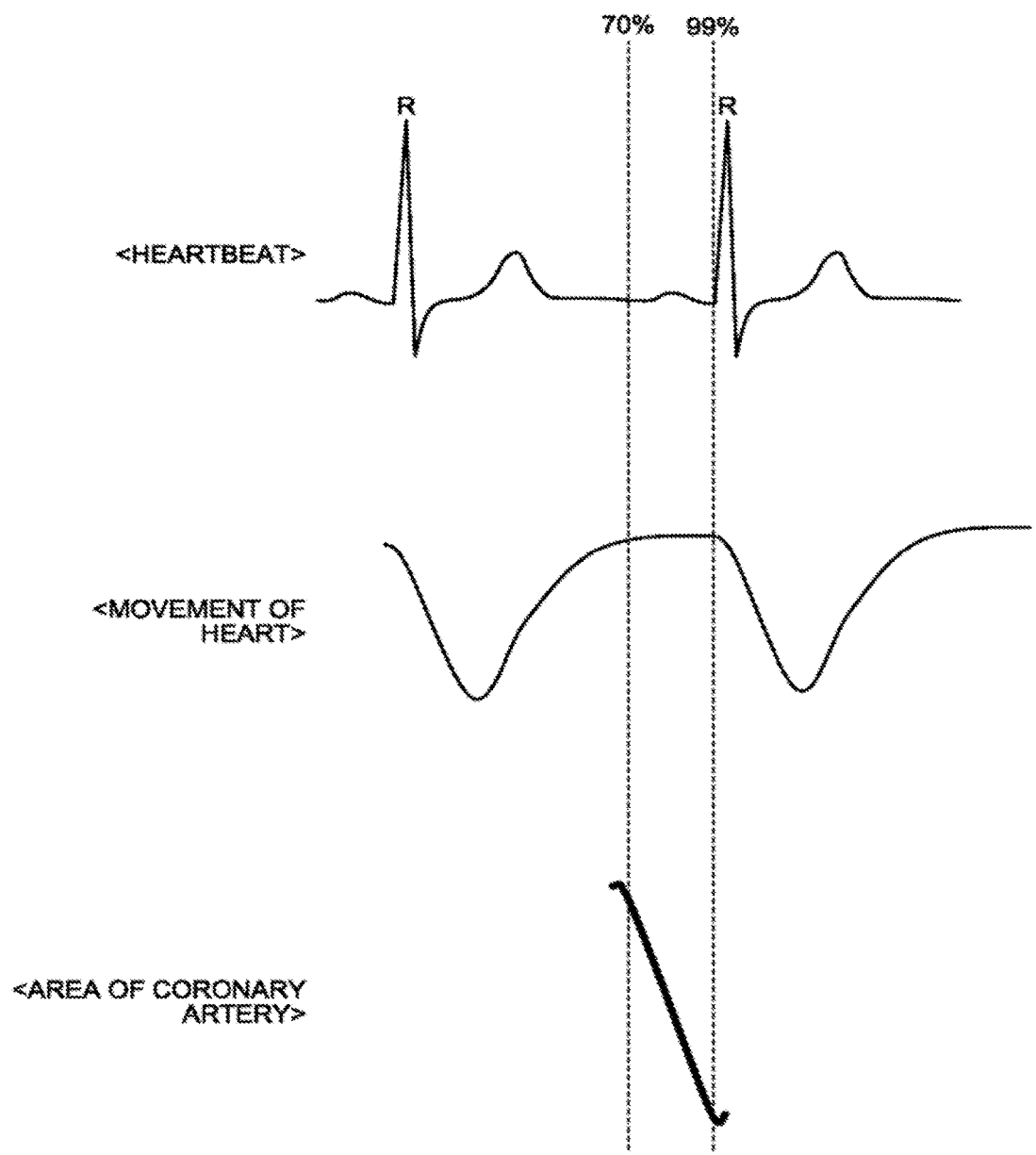
FIG. 4 is a diagram that illustrates the time phase that is used during fluid analysis according to the first embodiment.

FIG. 4 is a diagram that illustrates the time phase that is used for fluid analysis according to the first embodiment. In FIG. 4, the upper section indicates the heartbeat, the middle section indicates the movement of the heart, and the lower section indicates the area of the coronary artery. Furthermore, in FIG. 4, the horizontal direction indicates the time so that it represents time changes in the heartbeat, the movement of the heart, and the area of the coronary artery in a related manner. For example, the first calculation function 352 executes fluid analysis by using CT image data in the heart phase included in the range of the heart phases 70% to 99%. Here, as illustrated in FIG. 4, the heart phases 70% to 99% are time phases where there is not much movement in the heart and the area of the coronary artery is changed largely. The heart is moved due to expansion and contraction and, as illustrated in the middle section of FIG. 4, its movement becomes stable in the latter half (the heart phases 70% to 99%) of the expanding period. That is, the first calculation function 352 uses the CT image data in the heart phase included in the heart phases 70% to 99% where the movement is stable; thus, it may use CT image data where there are little movements in accordance with heartbeats. In the heart phases 70% to 99%, the relationship between the flow volume and the pressure within a blood vessel is a proportional relationship, and the first calculation function 352 uses the CT image data in the heart phases 70% to 99% as the CT image data in the wave-free period.

Furthermore, as illustrated in the lower section FIG. 4, the area of the coronary artery becomes largest in the vicinity of the heart phase 70%, and it becomes smallest in the vicinity of 99%. This is because the blood starts to flow into the coronary artery in the vicinity of the heart phase 70% and then the blood flows out as it comes closer to 99%. The first calculation function 352 uses CT image data in multiple time phases in the range of the heart phases 70% to 99% such that changes in the area of the coronary artery are included as much as possible; thus, analysis results are calculated with higher accuracy.

With reference back to FIG. 2, the second calculation function 353 extracts the structure of a blood vessel, included in medical image data, applies fluid analysis to the blood vessel structure so as to obtain a first index value, which is obtained on the basis of the pressure in a blood vessel on the upstream side of a predetermined position within the blood vessel and the relation equation between the volume of blood flow and the pressure in the blood vessel in a resting state, and a second index value, which is obtained on the basis of the pressure in the blood vessel on the downstream side of the predetermined position and the relation equation, and calculates the pressure ratio that is the ratio of the first index value to the second index value. For example, the second calculation function 353 uses the pressure at the time of zero flow volume, which indicates the pressure in a blood vessel in a case where the volume of blood flow within the blood vessel is zero, in the relation equation between the volume of blood flow and the pressure in the blood vessel to calculate the first index value and the second index value.

Specifically, in the time phase where the relationship between the volume of blood flow and the pressure in a blood vessel indicates a proportional relationship in the cardiac cycle of the subject in a resting state, the second calculation function 353 calculates the first index value, which is obtained on the basis of the pressure in a blood vessel on the upstream side of the predetermined position within the blood vessel and the pressure at the time of zero flow volume, which indicates the pressure in the blood vessel in a case where the volume of blood flow within the blood vessel is zero, and the second index value, which is obtained on the basis of the pressure in the blood vessel on the downstream side of the predetermined position and the pressure at the time of zero flow volume, and calculates the pressure ratio that is the ratio of the first index value to the second index value. More specifically, in the time phase where the relationship between the volume of blood flow and the pressure in a blood vessel in the cardiac cycle of the subject in a resting state indicates a proportional relationship, the second calculation function 353 calculates the pressure ratio of the pressure, which is based on the pressure on the upstream side of the predetermined position within a blood vessel and the pressure at the time of zero flow volume, which indicates the pressure in a case where the volume of blood flow within the blood vessel is zero, to the pressure, which is based on the pressure on the downstream side of the predetermined position and the pressure at the time of zero flow volume. That is, the second calculation function 353 performs a second calculation process to calculate the pressure ratio of the pressure, which is based on the pressure on the upstream side and the pressure at the time of zero flow volume, to the pressure, which is based on the pressure on the downstream side and the pressure at the time of zero flow volume.

Furthermore, when the second calculation process is performed, the second calculation function 353 calculates a first pressure ratio, which is the ratio of the pressure based on the pressure on the upstream side and the pressure at the time of zero flow volume to the pressure based on the pressure on the downstream side and the pressure at the time of zero flow volume, and a second pressure ratio, which is the ratio of the pressure based on the pressure on the upstream side and a predetermined pressure that is lower than the pressure at the time of zero flow volume to the pressure based on the pressure on the downstream side and the predetermined pressure. Specifically, the second calculation function 353 obtains the difference between the pressure in a blood vessel on the upstream side of the predetermined position within the blood vessel and the pressure at the time of zero flow volume as the first index value, obtains the difference between the pressure in a blood vessel on the downstream side of the predetermined position within the blood vessel and the pressure at the time of zero flow volume as the second index value, and calculates the pressure ratio, which is the ratio of the first index value to the second index value, as the first pressure ratio. Furthermore, the second calculation function 353 obtains a third index value, which is obtained based on the pressure in a blood vessel on the upstream side of the predetermined position within the blood vessel and a predetermined pressure that is lower than the pressure at the time of zero flow volume, obtains a fourth index value, which is obtained based on the pressure in the blood vessel on the downstream side of the predetermined position and the predetermined pressure, and calculates the pressure ratio, which is the ratio of the third index value to the fourth index value, as a second pressure ratio.

For example, the second calculation function 353 calculates the value of a first pressure index, which is based on the pressure on the upstream side of the lesion area (e.g., stenosis), the pressure on the downstream side, and the pressure at the time of zero flow volume, and the value of a second pressure index, which is based on the pressure on the upstream side, the pressure on the downstream side, and a predetermined pressure that is lower than the pressure at the time of zero flow volume. Here, the second calculation function 353 uses at least any one of the blood pressure of the right atrium and zero as the predetermined pressure, and it calculates, as the value of the second pressure index, at least any one of the ratio of the pressure based on the pressure on the upstream side and the pressure of the right atrium to the pressure based on the pressure on the downstream side and the pressure of the right atrium and the ratio of the pressure on the upstream side to the pressure on the downstream side.

An explanation is given below of the process performed by the second calculation function 353 as the second calculation process by using an example of the case where the first pressure ratio and the second pressure ratio are calculated. Here, the definition of the FFR is first explained. As described above, the FFR is defined by using the ratio of the flow volume in a case where there is no lesion to the flow volume in a case where there is a lesion, and it is calculated by using the following Equation (1). Furthermore, in Equation (1), "Qn" denotes the flow volume in a case where there is no lesion (e.g., stenosis), and "Qs" denotes the flow volume in a case where there is a lesion (e.g., stenosis).

$$FFR \equiv \frac{Qs}{Qn} \qquad (1)$$

As illustrated in Equation (1), for example, the FFR is defined by the equation where "Qs" is divided by "Qn". Here, adenosine is administered to the subject so that the maximum engorged state (stressed state) is obtained or the wave-free period in a resting state is targeted, whereby the relationship between the flow volume and the pressure within a blood vessel is a proportional relationship, and the FFR may be replaced with the definition of the pressure. That is, as the relationship between the flow volume and the pressure within a blood vessel is a proportional relationship, Equation (1) may be represented as the following Equation (2). Here, in Equation (2), "Pa" denotes the pressure on the upstream side of a lesion (e.g., stenosis), and "Pd" denotes the pressure on the downstream side of a lesion (e.g., stenosis). Furthermore, "Pv" denotes the pressure of the right atrium, to which venous blood flows from all over the body.

$$FFR \equiv \frac{Qs}{Qn} = \frac{Pd - Pv}{Pa - Pv} \qquad (2)$$

For example, as the relationship between the flow volume and the pressure within a blood vessel is a proportional relationship, "Qs" may be represented as "Pd−Pv" and "Qn" may be represented as "Pa−Pv", as illustrated in Equation (2). That is, the FFR is represented by using the ratio between the values that are obtained by subtracting the base line pressure of the blood vessel from the pressure on the upstream side of the lesion and the pressure on the downstream side thereof.

Here, in a stressed state where adenosine is administered to the subject, it may be considered that "Pa≫Pv" and "Pd≫Pv"; therefore, Equation (2) may be regarded as the following Equation (3).

$$FFR \equiv \frac{Qs}{Qn} = \frac{Pd - Pv}{Pa - Pv} \approx \frac{Pd}{Pa} \quad (3)$$

Specifically, as illustrated in Equation (3), FFR is calculated by using the equation that divides "Pd" by "Pa". In the actual clinical practice at present, the FFR or the instantaneous FFR is calculated from the measured "Pa" and "Pd" principally by using Equation (3).

Conversely, during calculation of the index value (the instantaneous FFR) intended for the subject in the resting state, the second calculation function 353 according to the first embodiment calculates a more accurate index value (new index value). For example, during non-invasive calculation of the index value intended for the subject in a resting state, the second calculation function 355 according to the first embodiment calculates a new index value and an index value that corresponds to the instantaneous FFR that is measured during the actual clinical practice. Specifically, during calculation of the instantaneous FFR by using the pressure that is calculated by the first calculation function 352, the second calculation function 353 calculates the instantaneous FFR (the first pressure index) that considers the pressure at the time of zero flow volume. Furthermore, in addition to the first pressure index, the second calculation function 353 calculates the instantaneous FFR (the second pressure index) that considers "Pa>>P0" and "Pd>>P0" or "Pv".

First, the FFR (the first pressure index) that considers the pressure at the time of zero flow volume is explained. The second calculation function 353 assigns the pressure on the upstream side of the lesion area, the pressure on the downstream side of the lesion area, and the pressure at the time of zero flow volume, calculated by the first calculation function 352, into the following Equation (4), thereby calculating the value of the first pressure index at each position of the blood vessel. Here, "Pa" in Equation (4) denotes the pressure on the upstream side of the lesion (e.g., stenosis), and "Pd" denotes the pressure on the downstream side of the lesion (e.g., stenosis). Furthermore, in Equation (4), "P0" denotes the pressure at the time of zero flow volume.

$$FFR \equiv \frac{Qs}{Qn} = \frac{Pd - P0}{Pa - P0} \quad (4)$$

For example, as illustrated in Equation (4), the second calculation function 353 calculates, as the first pressure index, the ratio between the values that are obtained by subtracting the pressure at the time of zero flow volume from the pressure on the upstream side of the lesion and the pressure on the downstream side. That is, the second calculation function 353 uses the pressure at the time of zero flow volume as the base line that is subtracted from the pressure on the upstream side of the lesion and the pressure on the downstream side. As described above, the pressure at the time of zero flow volume is the pressure in a blood vessel in a case where the flow volume in the blood vessel is "0". Therefore, as illustrated in Equation (4), "P0" is used, as the base line instead of the pressure "Pv" of the right atrium; thus, the proportional relationship between the flow volume and the pressure stay be represented with more accuracy as compared to a case where "Pv" is used.

Figure 5:
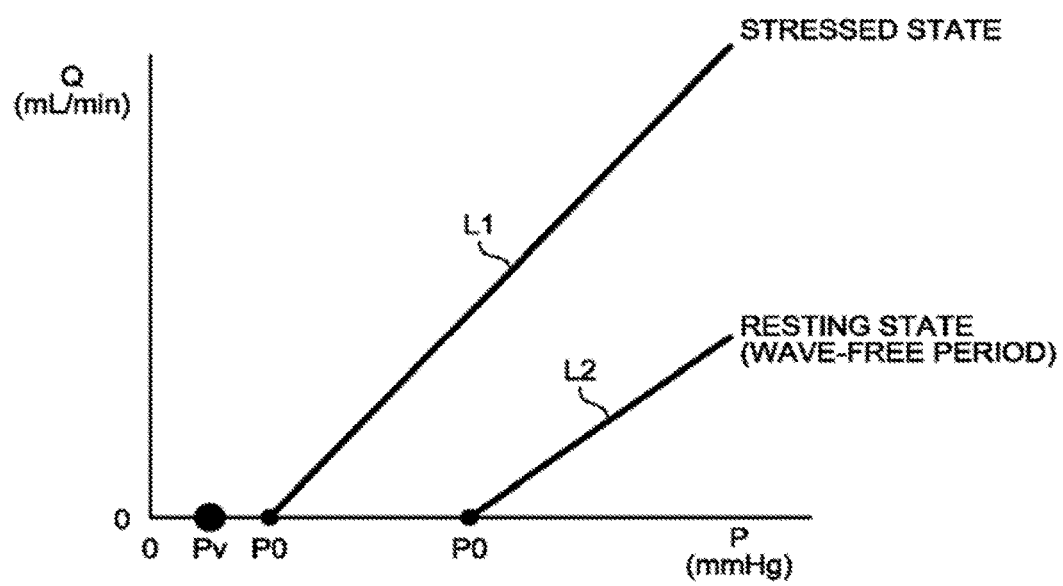
FIG. 5 is a graph that indicates the relationship between the flow volume and the pressure according to the first embodiment.

Here, the pressure "P0" at the time of zero flow volume is higher than the pressure "Pv" of the right atrium, and it indicates a different value during the wave-free period in a resting state and in a stressed state. FIG. 5 is a graph that illustrates the relationship between the flow volume and the pressure according to the first embodiment. Here, in FIG. 5, the horizontal axis indicates the pressure "P(mmHg)", and the vertical axis indicates the flow volume "Q(mL/min)". Furthermore, FIG. 5 illustrates a straight line L1, which indicates the relationship between the flow volume and the pressure in a stressed state in a case where the pressure "P0" at the time of zero flow volume is considered, and a straight line L2, which indicates the relationship between the flow volume and the pressure in a resting state in a case where the pressure "P0" at the time of zero flow volume is considered.

Figure 6:
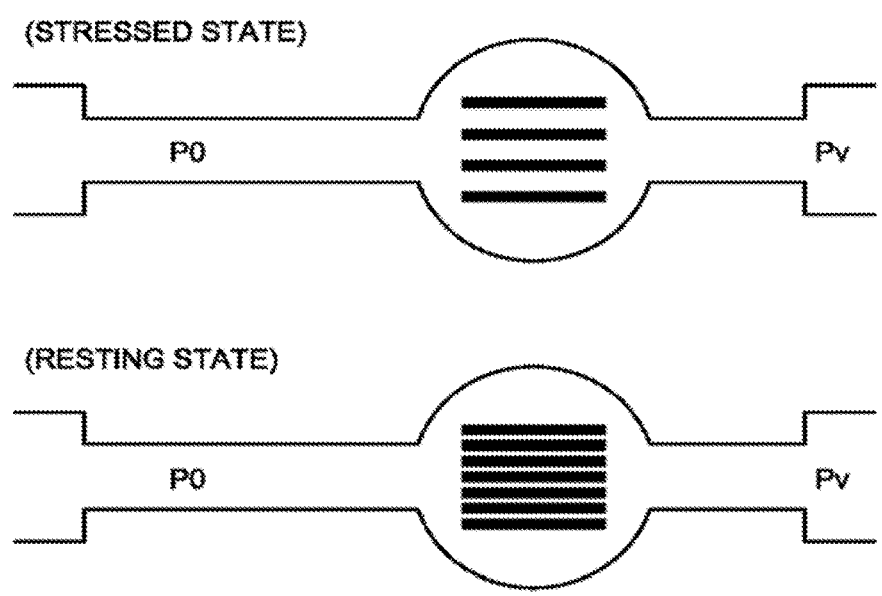
FIG. 6 is a diagram that illustrates a difference in the pressure at the time of zero flow volume between a stressed state and a resting state according to the first embodiment.

For example, aa illustrated in FIG. 5, the pressures "P0" at the time of zero flow volume in both the stressed state (the intercept of the straight line L1 at the side of P) and the resting state (the intercept of the straight line L2 at the side of P) indicate the values that are higher than "Pv". This is because there is a vascular resistance and even in the state of "P0>Pv" blood does not flow and the flow volume becomes zero. Furthermore, as illustrated in FIG. 5, "P0" during the wave-tree period in the resting state indicates a higher value than "P0" in the stressed state. This is because there is a difference in the heart muscle resistance between the stressed state and the resting state. FIG. 6 is a diagram that illustrates a difference in the pressure at the time of zero flow volume between the stressed state and the resting state according to the first embodiment. Here, FIG. 6 illustrates the relationship among "P0" in the stressed state and the resting state, "Pv", and the resistance.

For example, in a case where a blood vessel is expanded in a stressed state, as illustrated in FIG. 6, the resistance is decreased and therefore the value of "P0" at zero blood flow is closer to the value of "Pv" as compared to a resting state. Conversely, in the case of the resting state, as illustrated in FIG. 6, the resistance is large as compared to the stressed state and therefore the value of "P0" at zero blood flow is larger than the value of "Pv". Therefore, the relationship between the flow volume and the pressure in a case where the pressure "P0" at the time of zero flow volume is considered is different in the stressed state (the straight line L1) and in the resting state (the straight line L2), as illustrated in FIG. 5.

Here, as the medical-information processing apparatus 300 according to the present embodiment uses CT image data during the wave-free period in the resting state, the value of "P0" is larger than "P0" in the stressed state and, if it is considered that "Pa>>P0" axed "Pd>>P0", there is a possibility that the accuracy of calculation results is decreased. Therefore, as illustrated in Equation (4), the second calculation function 353 calculates the first pressure index in accordance with the equation that considers "P0". This allows the second calculation function 353 to calculate store accurate instantaneous FFR by using the equation that represents the relationship between the flow volume and the blood pressure with more accuracy.

Next, an explanation is given of the instantaneous FFR (the second pressure index) that considers "Pa>>P0" and "Pd>>P0" or "Pv". As described above, in the actual clinical practice at present, the instantaneous FFR is calculated principally by using Equation (3). Therefore, in addition to the first pressure index, the medical-information processing apparatus 300 according to the first embodiment calculates the second pressure index that corresponds to the instantaneous FFR that is calculated in the actual clinical practice at present. Specifically, the second calculation function 353 assumes that "Pa>>P0" and "Pd>>P0" and converts Equation (4) into the following Equation (5) to calculate the instantaneous FFR.

$$FFR \equiv \frac{Qs}{Qn} = \frac{Pd - P0}{Pa - P0} \approx \frac{Pd}{Pa} \qquad (5)$$

For example, the second calculation function 353 assigns the pressure on the upstream side of the lesion area and the pressure on the downstream side of the lesion area, calculated by the first calculation function 352, into Equation (5) to calculate the value of the second pressure index at each position of the blood vessel. Furthermore, the second calculation function 353 may calculate the instantaneous FFR that considers "Pv". That is, the second calculation function 353 assigns the pressure on the upstream side of the lesion area, calculated by the first calculation function 352, the pressure on the downstream side of the lesion area, and "Pv" into Equation (2) to calculate the value of the second pressure index at each position of the blood vessel.

Figure 7:
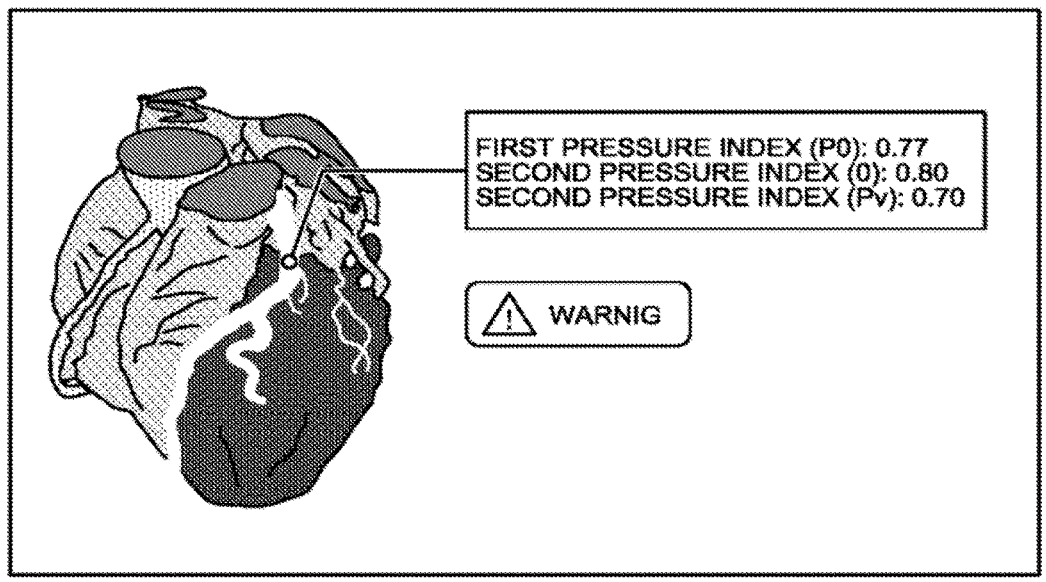
FIG. 7 is a diagram that illustrates an example of display by a presentation function according to the first embodiment.

With reference back to FIG. 2, the presentation function 354 presents the first pressure ratio and the second pressure ratio. Specifically, the presentation function 354 presents the value of the first pressure index and the value of the second pressure index, calculated by the second calculation function 353, on the display 340. FIG. 7 is a diagram that illustrates an example of display by the presentation function 354 according to the first embodiment. As illustrated in FIG. 7, the presentation function 354 causes the display 340 to present "the first pressure index (P0): 0.77", which is the value of the instantaneous FFR that considers the pressure at the time of zero flow volume, "the second pressure index (0): 0.80", which is the value of the instantaneous FFR where "P0≈0" in consideration of "Pa>>P0" and "Pd>>P0", and "the second pressure index (Pv): 0.70", which is the value of the instantaneous FFR that considers "Pv".

Here, as illustrated in FIG. 7, the presentation function 354 displays the value of the first pressure index and the value of the second pressure index, calculated by the second calculation function 353, at a corresponding position of the image of the blood vessel, generated on the basis of the CT image data that is used for fluid analysis. Here, the image of a blood vessel, presented by the display 340, may be an image that is generated by the X-ray CT apparatus 100, or it may be an image that is generated by the medical-information processing apparatus 300. Furthermore, if images of a blood vessel are generated, by the medical-information processing apparatus 300, the control function 351 performs image processing on CT image data, thereby generating images of a blood vessel. Furthermore, any images may be used as the image of a blood vessel, presented by the display 340, and for example volume rendering images, Curved Multi Planer Reconstruction (CPR) images, or Multi Planer Reconstruction (MPR) images, may be used.

Here, there may be a case where the value of the first pressure index and the value of the second pressure index are presented simultaneously, as illustrated in FIG. 7, or there may be a case where they are separately presented. In the case of separate presentation, for example, the input interface 330 receives a selection operation to select the presentation contents, and the presentation function 354 presents the value of the first pressure index our the value of the second pressure index on the display 340 in accordance with the selection operation. Furthermore, in addition to presentation of the value of the first pressure index and the value of the second pressure index on a single point, as illustrated in FIG. 7, the presentation function 354 may present it at a corresponding position of the image data in a related manner. For example, the presentation function 354 may present the value of the first pressure index and the value of the second pressure index at each position of the blood vessel, calculated by the second calculation function 355, such that they are related to each position of the blood vessel.

Furthermore, with regard to the method for presenting the value of the first pressure index and the value of the second pressure index, not only the presentation using numerical values, as illustrated in FIG. 7, but also presentation with any method may be conducted. For example, the presentation function 354 may assign a different color phase to each of the value of the first pressure index and the value of the second pressure index and display the presentation information that indicates changes in the value of each pressure index by using changes in the color phase. For example, the presentation function 354 assigns a different color phase to a different value of the first pressure index and displays the presentation image that indicates each position of the blood vessel on the image, illustrated in FIG. 7, in the color that corresponds to the value of the first pressure index. In the same manner, the presentation function 354 assigns a different color phase to a different value of the second pressure index. Furthermore, in accordance with the selection operation via the input interface 330, the presentation function 354 selects the presentation image that indicates each position of the blood vessel on the image in the color that corresponds to the selected pressure index.

Furthermore, the presentation function 354 presents alarm information in accordance with the value of the first pressure ratio and the value of the second pressure ratio. For example, the presentation function 354 presents the alarm information if there is a large difference between the value of the first pressure index and the value of the second pressure index. For example, the presentation function 354 presents the alarm information "WARNING", illustrated in FIG. 7, if the difference between the value of the first pressure index and the value of the second pressure index exceeds a predetermined threshold. Here, if the value of the first pressure index is compared with the value of the second pressure index, the presentation function 354 compares the first pressure index (P0) with either or both of the two second pressure indexes. Moreover, the predetermined threshold for each comparison may be arbitrarily set.

Furthermore, the presentation function 354 presents the alarm information if at least any one of the value of the first pressure index and the value of the second pressure index is equal to or less than the predetermined threshold. For example, the presentation function 354 refers to the threshold that is set for the first pressure index and the threshold that is set for the second pressure index and, if either one of them is equal to or less than the threshold, presents the alarm information "WARNING" that is illustrated in FIG. 7. Here, the threshold that is set for the first pressure index and the threshold that is set for the second pressure index may be arbitrarily set; there may be a case where the same value is used, or there may be a case where different values are used. Furthermore, there may be a case where the same value is used for the thresholds that are set for the two second pressure indexes, and there may be a case where different values are used.

Figure 8:
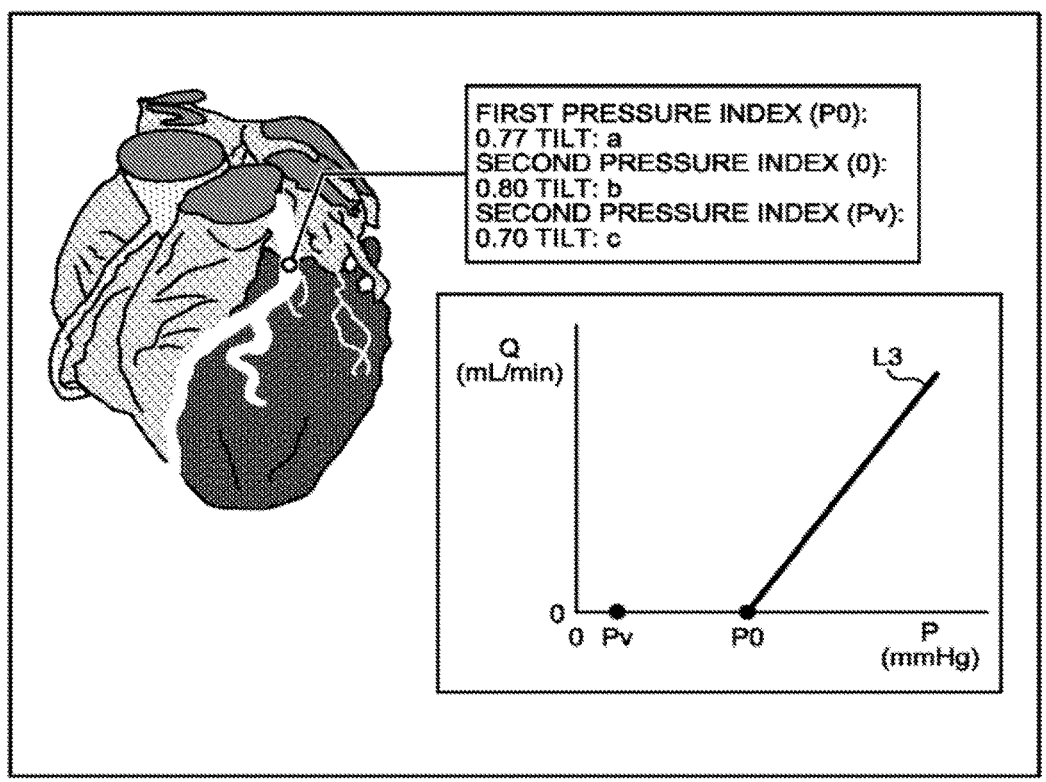
FIG. 8 is a diagram that illustrates an example of display by the presentation, function according to the first embodiment.
Figure 9:
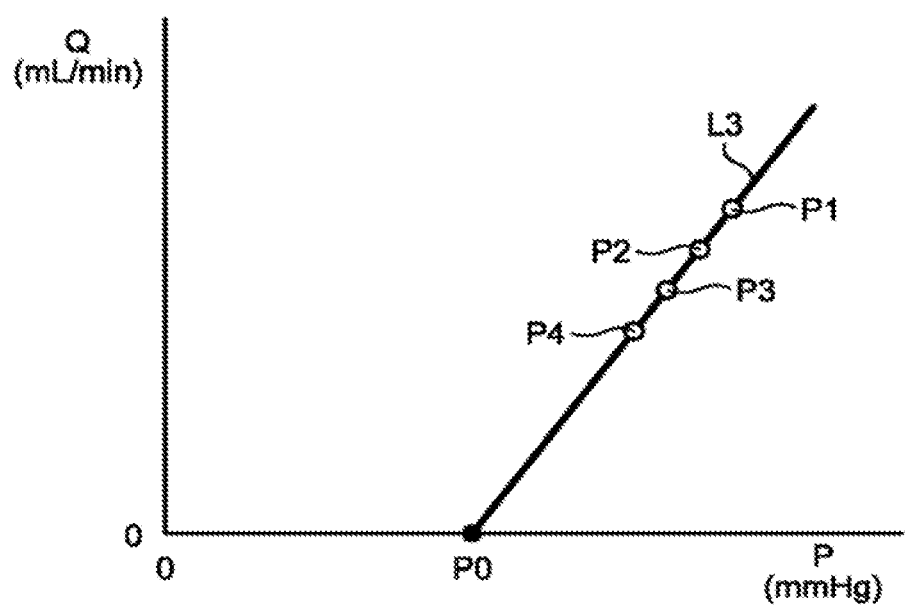
FIG. 9 is a diagram that illustrates an example of display by the presentation function according to the first embodiment.

Furthermore, the presentation function 354 may present the graph that indicates the flow volume and the pressure and the tilt of the graph. In such a case, the second calculation function 353 calculates the graph that indicates the relationship between the volume of blood flow and the pressure in the blood vessel in accordance with a result of fluid analysis by the first calculation function 352, and the presentation function 354 presents the calculated graph on the display 340. FIG. 8 is a diagram that illustrates an example of presentation by the presentation function 354 according to the first embodiment. For example, as illustrated in FIG. 8, the presentation function 354 causes the display 340 to present the graph that indicates the relationship between the flow volume "Q(mL/min)" and the pressure "P(mmHg)" in addition to "the first pressure index (P0): 0.77", "the second pressure index (0): 0.80", and "the second pressure index (Pv): 0.70". Furthermore, the presentation function 354 presents the value that indicates the tilt.

For example, the second calculation function 353 calculates a straight line L3, illustrated in FIG. 8, on the basis of time fluctuations in the flow volume, calculated by the first calculation function 352, time fluctuations in the pressure, and time fluctuations in the pressure at the time of zero flow volume. The presentation function 354 causes the display 340 to present the graph that is calculated by the second calculation function 353.

Furthermore, on the graph, the presentation function 354 may present the information that corresponds to the time phase of the image data that is used for fluid analysis. For example, on the graph, the presentation function 354 presents the value of the pressure in each time phase of the CT image data that is used for fluid analysis by the first calculation function 352. FIG. 5 is a diagram that illustrates an example of presentation by the presentation function 354 according to the first embodiment. For example, as illustrated in FIG. 5, the presentation function 354 causes the display 340 to present the information in which points P1 to P4, which indicate the values of the pressure at the same position in respective time phases, used for fluid analysis, are illustrated on the straight line L3.

In the above-described embodiment, an explanation is given of a case where the second calculation function 353 calculates the first pressure ratio "the first pressure index (P0)", which is a new index value, and the second pressure ratios "the second pressure index (Pv), the second pressure index (0)" in accordance with the actual clinical practice on the basis of a result of the fluid analysis by the first calculation function 352. However, embodiments are not limited thereto, and for example there may be a case where the second calculation function 353 calculates only "the first pressure index (P0)". Here, for calculation of "the first pressure index (P0)", not only results of the fluid analysis by the first calculation function 352 but also pressure values, invasively measured by using a pressure wire, may be used.

For example, in the case of using a pressure value that is measured by using a pressure wire, in the medical-information processing apparatus 300, the I/F circuitry 310 receives the pressure value on the upstream side of a predetermined position (e.g., a lesion area, such as stenosis) and the pressure value on the downstream side, measured by using a pressure wire (not illustrated). Then, the second calculation function 353 uses the pressure value on the upstream side and the pressure value on the downstream side, which have been received, and the pressure at the time of zero flow volume to calculate "the first pressure index (P0)" according to the above-described Equation (4). Here, any value may be used for the pressure at the time of zero flow volume; for example, there may be a case where the pressure at the time of zero flow volume, previously calculated by the first calculation function 352, is used or there may be a case where it is estimated from the state of a blood vessel of the subject.

Furthermore, for example, in the case of using results of fluid analysis by the first calculation function 352, the second calculation function 353 calculates "the first pressure index (P0)" according to the above-described Equation (4) by using the pressure value on the upstream side, the pressure value on the downstream side, and the pressure at the time of zero flow volume, calculated due to the fluid analysis. Then, the presentation function 354 causes the display 340 to present "the first pressure index (P0)" based on the pressure value, measured by using a pressure wire, and "the first pressure index (P0)" based on a result of the fluid analysis. In this manner, the medical-information processing apparatus 300 according to the first embodiment calculates "the first pressure index (P0)", thereby presenting a new index value that represents the proportional relationship between the flow volume and the pressure within a blood vessel with more accuracy, whereby the accuracy of diagnosis related to blood flow may be improved.

Figure 10:
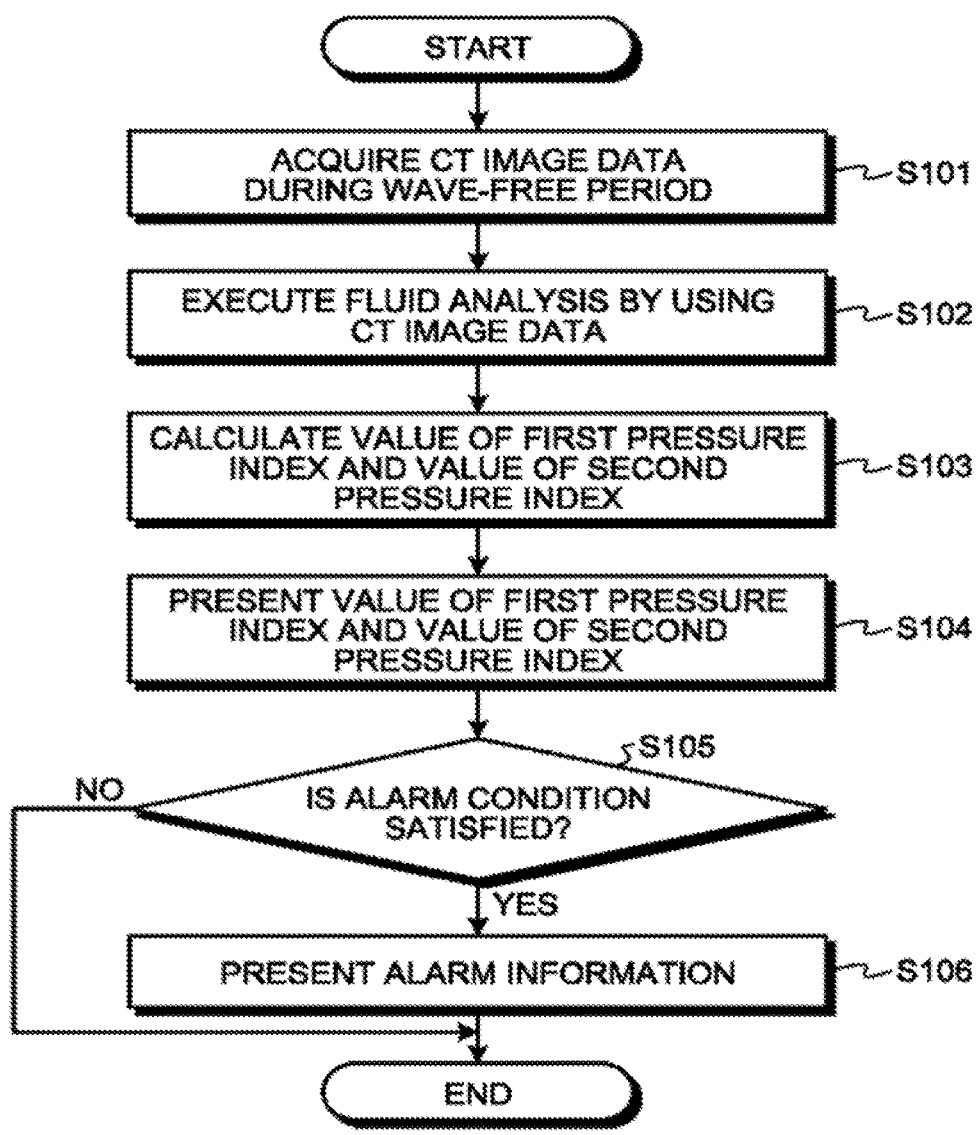
FIG. 10 is a flowchart that illustrates the steps of the process by the medical-information processing apparatus according to the first embodiment.

Next, an explanation is given of the steps of the process performed by the medical-information processing apparatus 300 according to the first embodiment. FIG. 10 is a flowchart that illustrates the steps of the process performed by the medical-information processing apparatus 300 according to the first embodiment. Here, Step S101 in FIG. 10 is implemented when for example the processing circuitry 350 invokes the program, corresponding to the control function 351, from the memory 320 and executes it. Furthermore, Step S102 is implemented when for example the processing circuitry 350 invokes the program, corresponding to the first calculation function 352, from the memory 320 and executes it. Furthermore, Step S103 is implemented when for example the processing circuitry 350 invokes the program, corresponding to the second calculation function 353, from the memory 320 and executes it. Moreover, Step S104 to Step S106 are implemented when for example the processing circuitry 350 invokes the program, corresponding to the presentation function 354, from the memory 320 and executes it.

In the medical-information processing apparatus 300 according to the present embodiment, the processing circuitry 350 first acquires CT image data in multiple time phases during the wave-free period from the CT image data that is collected in a resting state (Step S101). Then, the processing circuitry 350 executes fluid analysis by using the CT image data (Step S102) and calculates the value of the first pressure index and the value of the second pressure index (Step S103). Then, the processing circuitry 350 presents the value of the first pressure index and the value of the second pressure index, which have been calculated, on the display 340 (Step S104).

Then, the processing circuitry 350 determines whether the value of the first pressure index and the value of the second pressure index, which have been calculated, satisfy an alarm condition (Step S105). Here, if the alarm condition is satisfied (Yes at Step S105), the processing circuitry 350 presents the alarm information on the display 340 (Step S106). Conversely, if the alarm condition is not satisfied (No at Step S105), the processing circuitry 350 terminates the process.

As described above, according to the first embodiment, due to the fluid analysis that uses the image data that is collected in the time phase where the relationship between the volume of blood flow and the pressure in the blood vessel indicates a proportional relationship in the cardiac cycle of the subject in a resting state, the first calculation function 352 calculates the pressure on the upstream side of a lesion area within the blood vessel, the pressure on the downstream side of the lesion area, and the pressure at the time of zero flow volume, which indicates the pressure in a case where the volume of blood flow within the blood vessel is zero. The second calculation function 353 calculates the value of the first pressure index, which is the ratio of the pressure based on the pressure on the upstream side and the pressure at the time of zero flow volume to the pressure based on the pressure on the downstream side and the pressure at the time of zero flow volume, and the value of the second pressure index, which is the ratio of the pressure based on the pressure on the upstream side and a predetermined pressure, which is lower than the pressure at the time of zero flow volume, to the pressure based on the pressure on the downstream side and the predetermined pressure. The presentation function 354 presents the value of the first pressure index and the value of the second pressure index. Therefore, the medical-information processing apparatus 300 according to the first embodiment may calculate and present the value of the first pressure index, which represents the proportional relationship between the flow volume and the pressure within a blood vessel with more accuracy, and the value of the second pressure index, which corresponds to the invasively measured instantaneous FFR; thus, it is possible improve the accuracy of diagnosis that is conducted in a non-invasive manner.

For example, by referring to a more accurate value of the instantaneous FFR as well as referring to the value of the instantaneous FFR in accordance with the actual clinical practice at present, comparison results between the value of the first pressure index and the value of the second pressure index may be used for diagnosis. For example, if the value of the first pressure index and the value of the second pressure index are similar values, it may be considered that the numerical values have a high reliability, and treatments or the like may be conducted due to diagnosis based on the calculated value. Conversely, if there is a large difference between the value of the first pressure index and the value of the second pressure index, it may be recommended that invasive FFR measurement is conducted.

Furthermore, according to the first embodiment, the second calculation function 353 uses at least any one of the blood pressure of the right atrium and zero as a predetermined pressure to calculate, as the value of the second pressure index, at least any one of the ratio of the pressure based on the pressure on the upstream side and the pressure of the right atrium to the pressure based on the pressure on the downstream side and the pressure of the right atrium and the ratio of the pressure on the upstream side to the pressure can the downstream side. Therefore, the medical-information processing apparatus 300 according to the first embodiment may calculate and present the value of the instantaneous FFR where "P0≈0" in consideration of "Pa>>P0" and "Pd>>P0" and the value of the instantaneous FFR in consideration of "Pv", and it may handle a case where any one of the values is used during the actual clinical practice.

Furthermore, according to the first embodiment, the presentation function 354 presents alarm information on the basis of the value of the first pressure index and the value of the second pressure index. For example, the presentation function 354 presents the alarm information if the difference between the value of the first pressure index and the value of the second pressure index exceeds a predetermined threshold. Furthermore, the presentation function 354 presents the alarm information if at least any one of the value of the first pressure index and the value of the second pressure index is equal to or less than a predetermined threshold. Therefore, the medical-information processing apparatus 300 according to the first embodiment may present the alarm that corresponds to the calculation result and prompt the observer to pay attention.

Furthermore, according to the first embodiment, the second calculation function 353 calculates the graph that indicates the relationship between the volume of blood flow and the pressure in the blood vessel in accordance with an analysis result of the fluid analysis, and the presentation function 354 presents the graph. Furthermore, the second calculation function 353 calculates the tilt of the graph, and the presentation function 354 presents the tilt. Furthermore, on the graph, the presentation function 354 presents the information that corresponds to the time phase of the image data that is used for fluid analysis. Therefore, the medical-information processing apparatus 300 according to the first embodiment may present analysis information to observers.

Second Embodiment

In the above-described first embodiment, an explanation is given of a case where the value of the first pressure index that considers the pressure "P0" at the time of zero flow volume is calculated and presented. In a second embodiment, an explanation is given of a case where the value of the first pressure index is not calculated, and only the value of the second pressure index is calculated and presented. Furthermore, the configuration of the medical-information processing apparatus 300 according to the second embodiment is basically the same as the configuration of the medical-information processing apparatus 300 that is illustrated in FIG. 2. Therefore, the different aspect from the medical-information processing apparatus 300 according to the first embodiment is primarily explained below, and the component that performs the same function as that illustrated in FIG. 2 is attached with the same reference numeral, and detailed explanation is omitted.

The first calculation function 352 according to the second embodiment calculates the pressure on the upstream side of a lesion area within a blood vessel and the pressure on the downstream side of the lesion area due to fluid analysis that uses the image data that is collected in the time phase where the relationship between the volume of blood flow and the pressure in the blood vessel indicates a proportional relationship in the cardiac cycle of the subject in a resting state. That is, the first calculation function 352 in the medical-information processing apparatus 300 according to the second embodiment calculates the indexes related to the blood flow, including the pressure "Pa" on the upstream side of the lesion area and the pressure "Pd" on the downstream side due to fluid analysis without calculating the pressure "P0" at the time of zero flow volume, which is calculated according to the first embodiment.

The second calculation function 353 according to the second embodiment calculates the first pressure ratio ("the second pressure index (Pv)" according to the first embodiment), which is the ratio of the pressure based on the pressure on the upstream side and the pressure of the right atrium to the pressure based on the pressure on the downstream side and the pressure of the right atrium, and the second pressure ratio ("the second pressure index (0)" according to the first embodiment), which is the ratio of the pressure on the upstream side to the pressure on the downstream side.

The presentation function 354 according to the second embodiment presents "the second pressure index (Pv)" and "the second pressure index (0)" on the display 340. Here, the presentation function 354 according to the second embodiment may make various presentations as is the case with the first embodiment.

Figure 11:
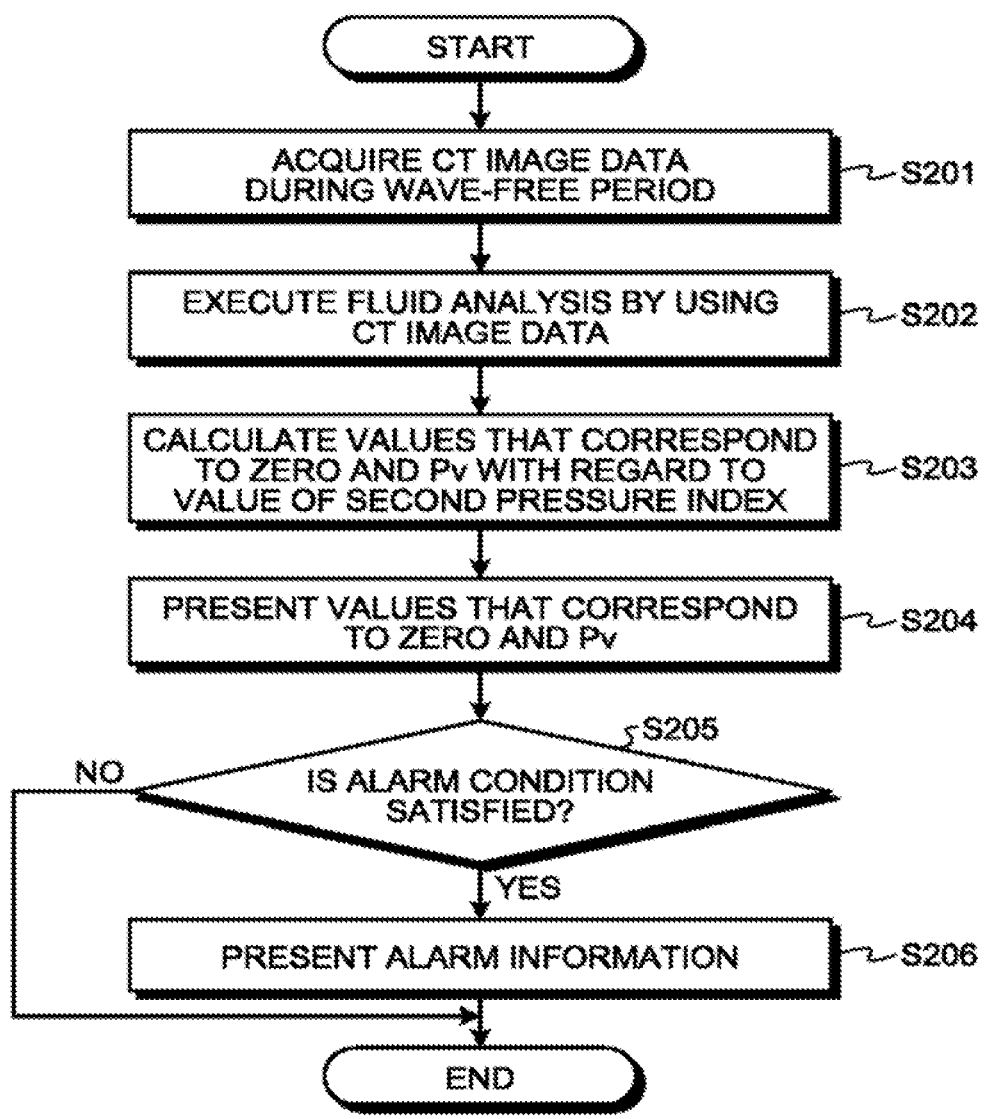
FIG. 11 is a flowchart that illustrates the steps of the process by the medical-information processing apparatus according to a second embodiment.

Next, an explanation is given of the steps of the process performed by the medical-information processing apparatus 300 according to the second embodiment. FIG. 11 is a flowchart that illustrates the steps of the process performed by the medical-information processing apparatus 300 according to the second embodiment. Here, Step S201 in FIG. 11 is implemented when for example the processing circuitry 350 invokes the program, corresponding to the control function 351, from the memory 320 and executes it. Furthermore, Step S202 is implemented when for example the processing circuitry 350 invokes the program, corresponding to the first calculation function 352, from the memory 320 and executes it. Furthermore, Step S203 is implemented when for example the processing circuitry 350 invokes the program, corresponding to the second calculation function 353, from the memory 320 and executes it. Moreover, Step S204 to Step S206 are implemented when for example the processing circuitry 350 invokes the program, corresponding to the presentation function 354, from the memory 320 and executes it.

In the medical-information processing apparatus 300 according to the present embodiment, the processing circuitry 350 first acquires CT image data in multiple time phases during the wave-free period from the CT image data that is collected in a resting state (Step S201). Then, the processing circuitry 350 executes fluid analysis by using the CT image data (Step S202) and calculates each of the values that correspond to zero and Pv with regard to the value of the second pressure index (Step S203). Then, the processing circuitry 350 presents the calculated values, which correspond to zero and Pv, with regard to the value of the second pressure index on the display 340 (Step S204).

Then, the processing circuitry 350 determines whether the calculated value of the second pressure index satisfies the alarm condition (Step S205). Here, if the alarm condition is satisfied (Yes at Step S205), the processing circuitry 350 presents the alarm information on the display 340 (Step S206). Conversely, if the alarm condition is not satisfied (No at Step S205), the processing circuitry 350 terminates the process.

As described above, according to the second embodiment, the first calculation function 352 calculates the pressure on the upstream side of a lesion area within a blood vessel and the pressure on the downstream side of the lesion area due to the fluid analysis that uses the image data that is collected in the time phase where the relationship between the volume of blood flow and the pressure in the blood vessel indicates a proportional relationship in the cardiac cycle of the subject in a resting state. The second calculation function 353 calculates the value of the second pressure index (Pv), which is the ratio of the pressure based on the pressure on the upstream side and the pressure of the right atrium to the pressure based on the pressure on the downstream side and the pressure of the right atrium, and the value of the second pressure index (0), which is the ratio of the pressure on the upstream side to the pressure on the downstream side. The presentation function 354 presents the value of the second pressure index (Pv) and the value of the second pressure index (0). Therefore, the medical-information processing apparatus 300 according to the second embodiment may present the value of the instantaneous FFR where "P0≈0" in consideration of "Pa>>P0" and "Pd>>P0" and the value of the instantaneous FFR in consideration of "Pv" with regard to the instantaneous FFR that is used during the actual clinical practice at present, whereby the accuracy of non-invasive diagnosis may be improved.

Third Embodiment

Furthermore, although the first and second embodiments have been explained above, various different embodiments may be implemented other than the above-described first and second embodiments.

In the above-described embodiment, an explanation is given of a case where the instantaneous FFR is calculated for CT image data as the target. However, embodiments are not limited thereto, and there may be a case where different medical image data, such as angiography images, are the target.

Furthermore, in the above-described embodiment, an explanation is given of a case where the pressure "P0" at the time of zero flow volume is calculated during the fluid analysis that uses image data in multiple time phases. However, embodiments are not limited thereto, and there may be a case where the pressure "P0" at the time of zero flow volume is acquired by using other techniques. For example, there may be a case where an empirical value, or the like, is used as the pressure "P0" at the time of zero flow volume. In such a case, for example, the second calculation function 353 calculates the first index value and the second index value by using the previously stored value of the pressure "P0" at the time of zero flow volume or the value of the pressure "P0" at the time of zero flow volume, which is input via an input interface.

Furthermore, there may be a case where the pressure "P0" at the time of zero flow volume is estimated from sites other than the heart. In such a case, for example, the first calculation function 352 estimates one pressure "P0" at the time of zero flow volume in the coronary artery on the basis of the relationship between the volume of blood flow in a blood vessel of a site other than the heart and the pressure in the blood vessel.

Furthermore, in the above-described embodiment, an explanation is given of a case where image data in multiple time phases is used. However, embodiments are not limited thereto, and there may be a case where the pressure "P0" at the time of zero flow volume is estimated from image data in a single time phase. In such a case, for example, the first calculation function 352 estimates the pressure "P0" at the time of zero flow volume by applying multiple times of fluid analysis to the image data on the heart in a single time phase.

Furthermore, as the method for estimating the pressure "P0" at the time of zero flow volume from the image data in a single time phase, for example, there may be a case where the pressure "P0" art the time of zero flow volume is estimated on the basis of vascular resistance. In such a case, for example, the first, calculation function 352 estimates the pressure "P0" at the time of zero flow volume on the basis of the resistance in the coronary artery and the resistance in the heart muscle.

For example, the first calculation function 352 calculates the pressure in a blood vessel of the coronary artery and the vascular resistance due to fluid analysis that uses image data in a single time phase. Then, the first calculation function 352 acquires the value of the heart muscle resistance via an external input, or the like, and calculates the resistance value of the coronary artery, with which the volume of blood flow is zero, while variously changing the value of resistance in the coronary artery in relation to the acquired value of the heart muscle resistance. Furthermore, the first calculation function 352 estimates the pressure "P0" at the time of zero flow volume on the basis of the pressure in a blood vessel of the coronary artery and the vascular resistance, obtained due to the fluid analysis, and the resistance value of the coronary artery, with which the volume of blood flow is zero.

Furthermore, in the above-described embodiment, an explanation is given of a case where the relation equation between the volume of blood flow and the pressure in the blood vessel is derived on the basis of the pressure "P0" at the time of zero flow volume. However, embodiments are not limited thereto, and it may be derived by using various different methods. For example, there may be a case where the relation equation between the volume of blood flow and the pressure in the blood vessel is derived by using the value of the pressure at the same position in each time phase in the image data in multiple time phases, used for fluid analysis. In such a case, as the relation equation between the volume of blood flow and the pressure in the blood vessel, for example, the first calculation function 352 calculates the straight line that approximates the value of the pressure at the same position in each of the time phases (e.g., 4 time phases).

Furthermore, for example, the first calculation function 352 may also derive the relation equation between the volume of blood flow and the pressure in the blood vessel by using flow volume "Q0" at the time of zero pressure, which indicates the volume of blood flow in a case where the pressure in the blood vessel is zero. Specifically, the first calculation function 352 calculates the value of the intercept at the side of Q of the straight line L2 in the graph of FIG. 5 due to fluid analysis and derives the relation equation between the volume of blood flow and the pressure in the blood vessel by using the calculated value.

Furthermore, in the above-described embodiment, an explanation is given of the case of the use of image data in the time phase where the relationship between the volume of blood flow and the pressure in the blood vessel indicates a proportional relationship in the cardiac cycle of the subject in a resting state. However, the embodiment is not limited thereto, and it is applicable if the relationship between the volume of blood flow and the pressure in the blood vessel in a resting state is an already-known state. That is, even if the relationship between the volume of blood flow and the pressure in the blood vessel is not a proportional relationship, it is acceptable if the relationship is already known.

In such a case, the control function 351 acquires image data that is obtained during imaging on the subject in a state where the relationship between the volume of blood flow and the pressure in the blood vessel in the cardiac cycle of the subject is already known. The second calculation function 353 extracts the structure of a blood vessel, included in the image data, and applies fluid analysis to the structure of the blood vessel to obtain the first index value, which is obtained on the basis of the pressure in the blood vessel on the upstream side of the predetermined position within the blood vessel and the relation equation between the volume of blood flow and the pressure in the blood vessel in a resting state, and the second index value, which is obtained on the basis of the pressure in the blood vessel on the downstream side of the predetermined position and the relation equation, and calculates the pressure ratio, which is the ratio of the first index value to the second index value. For example, the second calculation function 353 calculates the first index value and the second index value in accordance with the relation equation that is modelled by another function that indicates the relationship between the volume of blood flow and the pressure in the blood vessel.

Furthermore, in the above-described embodiment, an explanation is given of an example of the case where a blood vessel of the heart is the target for analysis. However, embodiments are not limited thereto, and there may be a case where for example the pulmonary artery is the target for analysis. In such a case, the used image data is obtained during imaging on the subject in a state where the relationship between the volume of blood flow and the pressure in the blood vessel in the pulmonary artery is already known. For example, the used image data is in the time phase where the relationship between the volume of blood flow and the pressure in a blood vessel in the pulmonary artery is a proportional relationship.

Figure 12:
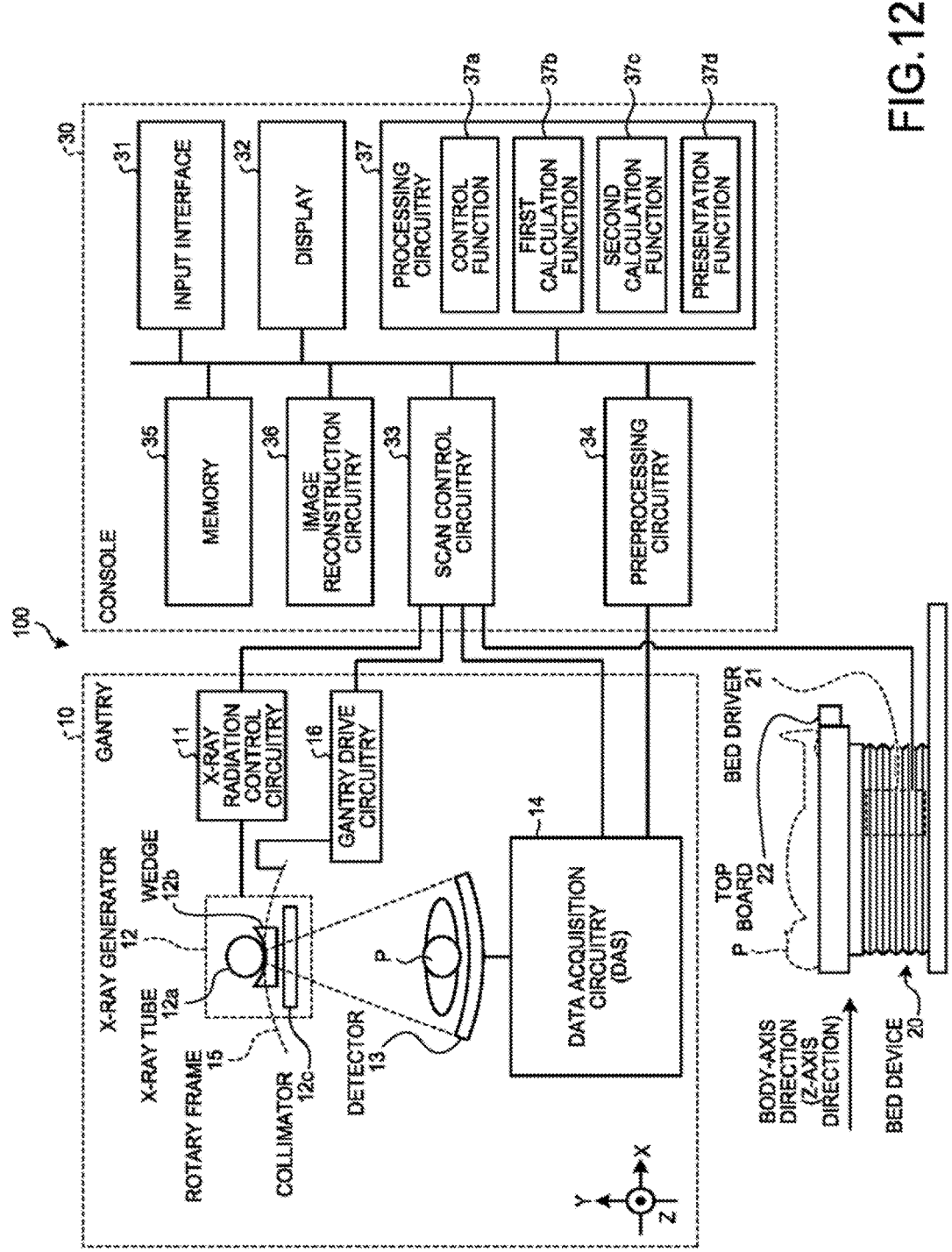
FIG. 12 is a diagram that illustrates an example of the configuration of an X-ray CT apparatus according to a third embodiment.

Furthermore, in the above-described embodiment, an explanation is given of a case where the medical-information processing apparatus 300 performs various processes. However, embodiments are not limited thereto, and for example there may be a case where the X-ray CT apparatus 100 performs various processes. FIG. 12 is a diagram that illustrates an example of the configuration of the X-ray CT apparatus 100 according to a third embodiment.

As illustrated in FIG. 12, the X-ray CT apparatus 100 according to the third embodiment includes a gantry 10, a bed apparatus 20, and a console 30. The gantry 10 is a device that emits X-rays to a subject P, detects the X-rays that are transmitted through the subject P, and outputs them to the console 30, and it includes X-ray radiation control circuitry 11, an X-ray generator 12, a detector 13, a data acquisition circuitry (DAS: Data Acquisition System) 14, a rotary frame 15, and gantry drive circuitry 16.

The rotary frame 15 is an annular frame that supports the X-ray generator 12 and the detector 13 such that they are opposed to each other with the subject P interposed therebetween and that is rotated at high speed in a circular orbit around the subject P by the gantry drive circuitry 16 that is described later.

The X-ray radiation control circuitry 11 supplies a high voltage to an X-ray tube 12a by controlling an undepicted high-voltage generator, and the X-ray tube 12a generates X-rays by using the high voltage that is supplied from the undepicted high-voltage generator. Under the control of scan control, circuitry 33, which is described later, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, according to the present embodiment, there may be a case where multiple types of wedges 12b are manually switched by an operator.

The X-ray generator 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the undepicted high-voltage generator, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+ the fan angle) that enables a half reconstruction. Furthermore, under the control of the X-ray radiation control circuitry 11, the X-ray tube 12a is capable of intermittently emitting X-rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or bow-tie filter.

The collimator 12c is a slit that narrows the irradiation range of X-rays, of which the amount of X-rays has been adjusted by the wedge 12b, under the control of the X-ray radiation control circuitry 11 that is described later.

The gantry drive circuitry 16 drives and rotates the rotary frame 15 so that the X-ray generator 12 and the detector 13 are rotated in a circular orbit around the subject P.

The detector 13 is a two-dimensional array-type detector (plane detector) that detects X-rays, transmitted through the subject P, and detecting element columns, which include X-ray detecting elements corresponding to multiple channels, are arranged in multiple columns along the Z-axis direction. Specifically, the detector 13 includes X-ray detecting elements that are arranged in multiple columns, e.g., 320 columns, along the Z-axis direction, and it is capable of detecting X-rays, transmitted through the subject P, within a wide range, such as the range that includes the lung or the heart of the subject P. Here, the Z axis represents the direction of the central axis of rotation of the rotary frame 15 in a state where the gantry 10 is not tilted.

The data acquisition circuitry 14 is a DAS, and it acquires projection data from the detection data on X-rays that are detected by the detector 13. For example, the data acquisition circuitry 14 performs amplification process, A/D conversion process, inter-channel sensitivity correction process, or the like, on the X-ray intensity distribution data, detected by the detector 13, to generates projection data and transmits the generated projection data to the console 30 that is described later. For example, if X-rays are continuously emitted from the X-ray tube 12a while the rotary frame 15 is rotated, the data acquisition circuitry 14 acquires the group of projection data for the entire periphery (360 degrees). Furthermore, the data acquisition circuitry 14 transmits each acquired projection data in relation to the tube position to the console 30 that is described later. The tube position is the information that indicates the projection direction of the projection data. Moreover, the inter-channel sensitivity correction process may be performed by preprocessing circuitry 34 that is described later.

The bed device 20 is a device on which the subject P is placed and, as illustrated in FIG. 12, it includes a bed driver 21 and a top board 22. The bed driver 21 moves the top board 22 in the direction of the Z axis to move the subject P into the rotary frame 15. The top board 22 is a board on which the subject P is placed. Furthermore, in the present embodiment, an explanation is given of a case where the relative position between the gantry 10 and the top board 22 is changed by controlling the top board 22; however, embodiments are not limited thereto. For example, if the gantry 10 is self-propelling, the relative position between the gantry 10 and the top board 22 may be changed, by controlling driving of the gantry 10.

Furthermore, for example, the gantry 10 conducts helical scan to scan the subject P in a helical fashion by rotating the rotary frame 15 while the top board 22 is moved. Alternatively, the gantry 10 conducts conventional scan to scan the subject P in a circular orbit by rotating the rotary frame 15 with the position of the subject P fixed after the top board 22 is moved. Alternatively, the gantry 10 implements a step-and-shoot method to conduct conventional scan at multiple scan areas by moving the position of the top board 22 at a constant interval.

The console 30 is a device that receives an operation of the X-ray CT apparatus 100 from an operator and that reconstructs CT image data by using the projection data that is acquired by the gantry 10. As illustrated in FIG. 12, the console 30 includes an input interface 31, a display 32, the scan control circuitry 33, the preprocessing circuitry 34, a memory 35, image reconstruction circuitry 36, and processing circuitry 37.

The input interface 31 includes a mouse, keyboard, trackball, switch, button, joystick, or the like, which is used by an operator of the X-ray CT apparatus 100 to input various commands or various settings, and it transfers eke information on the command or setting, received from the operator, to the processing circuitry 37. For example, the input interface 31 receives, from an operator, a capturing condition for CT image data, a reconstruction condition for reconstructing CT image data, an image processing condition for CT image data, or the like. Furthermore, the input interface 31 receives an operation to select an examination for the subject P. Moreover, the input interface 31 receives a designation operation to designate a site on the image.

The display 32 is a monitor that is viewed by an operator and, under the control of the processing circuitry 37, if displays the image data, generated from CT image data, to the operator or displays a graphical user interface (GUI) for receiving various commands, various settings, or the like, from the operator via the input interface 31. Furthermore, the display 32 presents the planning screen for scan plan, the screen during scan, or the like.

The scan control circuitry 33 controls operations of the X-ray radiation control circuitry 11, the gantry drive circuitry 16, the data acquisition circuitry 14, and the bed driver 21 under the control of the processing circuitry 37, thereby controlling the process to acquire projection data by the gantry 10. Specifically, the scan control circuitry 33 controls the process to acquire projection data during capturing for collecting positioning images (scano images) and during the primary capturing (scan) for collecting images used for diagnosis.

The preprocessing circuitry 34 performs correction processing, such as logarithmic conversion processing, offset correction, sensitivity correction, or beam hardening correction, on the projection data that is generated by the data acquisition circuitry 14, thereby generating corrected projection data. Specifically, the preprocessing circuitry 34 generates corrected projection data with regard to each piece of projection data on positioning images, generated by the data acquisition circuitry 14, and projection data collected during the primary capturing, and stores it in the memory 35.

The memory 35 stores the projection data that is generated by the preprocessing circuitry 34. Specifically, the memory 35 stores the projection data on positioning images, generated by the preprocessing circuitry 34, and the projection data for diagnosis, collected during the primary capturing. Furthermore, the memory 35 stores CT image data, or the like, which is reconstructed by the image reconstruction circuitry 36 that is described later. Moreover, the memory 35 appropriately stores processing results of the processing circuitry 57 that is described later.

The image reconstruction circuitry 36 reconstructs CT image data by using the projection data that is stored in the memory 35. Specifically, the image reconstruction circuitry 36 reconstructs CT image data from the projection data on positioning images and from the projection data on images that are used for diagnosis. Here, the reconstruction method includes various methods, and it may be, for example, back projection processing. Furthermore, the back projection processing may include, for example, back projection processing by using a filtered back projection (FBP) method. Alternatively, the image reconstruction circuitry 36 may also use a successive approximation technique to reconstruct CT image data.

Furthermore, the image reconstruction circuitry 36 conducts various types of image processing on CT image data, thereby generating image data. Then, the image reconstruction circuitry 36 stores, in the memory 35, the reconstructed CT image data or the image data that is generated during various types of image processing.

The processing circuitry 37 controls operations of the gantry 10, the bed device 20, and the console 30, thereby performing the overall control on the X-ray CT apparatus 100. Specifically, the progressing circuitry 37 controls the scan control circuitry 33 so as to control CT scan that is conducted by the gantry 10. Furthermore, the processing circuitry 37 controls the image reconstruction circuitry 36 so as to control an image reconstruction process or an image generation process in the console 30. Furthermore, the processing circuitry 37 performs control such that various types of image data, stored in the memory 35, are displayed on the display 32.

Furthermore, as illustrated in FIG. 12, the processing circuitry 37 performs a control function 37a, a first calculation function 37b, a second calculation function 37c, and a presentation function 37d. The control function 37a performs overall control of the X-ray CT apparatus 100. The first calculation function 37b performs the same process as that of the above-described first calculation function 352. The second calculation function 37c performs the same process as that of the above-described second calculation function 353. The presentation function 37d performs the same process as that of the above-described presentation function 354.

In the above-described embodiment, an explanation is given of an example of the case where each processing function is implemented by a single processing circuit (the processing circuitry 350 and the processing circuitry 37); however, embodiments are not limited thereto. For example, the processing circuitry 350 and the processing circuitry 37 may be configured by combining multiple independent processors so that each of the processors executes each program to implement each processing function. Furthermore, each processing function, provided by the processing circuitry 350 and the processing circuitry 37, may be implemented by being appropriately separated from or combined into one or more processing circuits.

Furthermore, the term "processor", used in the explanation of each of the above-described embodiments, means for example a central processing unit (CPU), a graphics processing unit (GPU), or a circuit, such as an application specific integrated circuit (ASIC), or a programmable logic device (e.g., a simple programmable logic device (SPLD), a complex programmable logic device (CPLD), or a field programmable gate array (FPGA)). Here, a configuration may be such that, instead of storing a program in the memory, a program is directly installed in a circuit of the processor. In this case, the processor reads and executes the program, installed in the circuit, to perform the function. Furthermore, with regard to each of the processors according to the present embodiment, as well as the case where each processor is configured as a single circuit, multiple independent circuits may be combined to be configured as a single processor to implement the function.

Here, the programs that are executed by the processor are provided by being previously installed in a read only memory (ROM), a memory, or the like. Furthermore, the programs may be provided by being recorded in a storage medium, readable by a computer, such as compact disk (CD)-ROM, flexible disk (FD), CD-R (recordable), or digital versatile disk (DVD), in the form of file installable or executable by the device. Furthermore, the program may be stored in a computer, connected via a network, such as the Internet, and provided or distributed by being downloaded via the network. For example, the program is configured as a module that includes each functional unit. In the actual hardware, the CPU reads the program from a storage medium, such as a ROM, and executes it so that each module is loaded into the primary storage device and is generated on the primary storage device.

According to at least one of the above-described embodiments, the accuracy of diagnosis related to blood flow may be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical-information processing apparatus comprising processing circuitry configured to acquire medical image data including a medical image that is obtained during imaging on a subject in a resting state in a time phase where a relationship between a volume of blood flow and a pressure in a blood vessel in a cardiac cycle of the subject indicates a proportional relationship, extract a structure of the blood vessel of the subject, included in the medical image data, obtain, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel, calculate a first pressure ratio that is a ratio of the first index value to the second index value, and a second pressure ratio that is a ratio of the third index value to the fourth index value, and present the first pressure ratio and the second pressure ratio on a display.

2. The medical-information processing apparatus according to claim 1, wherein the processing circuitry is configured to calculate the pressures in the blood vessel on the upstream side and on the downstream side and the pressure at the time of zero flow volume.

3. The medical-information processing apparatus according to claim 1, wherein the processing circuitry is configured to obtain the second index value and the first pressure ratio with regard to each of positions on the downstream side, and present, on the display, the first pressure ratio at each of the positions on the downstream side together with the medical image data in a manner of being related to a corresponding position in the medical image data.

4. The medical-information processing apparatus according to claim 1, wherein the processing circuitry is configured to obtain a difference between the pressure in the blood vessel on the upstream side of the predetermined position within the blood vessel and the pressure at the time of zero flow volume as the first index value, obtain a difference between the pressure in the blood vessel on the downstream side of the predetermined position within the blood vessel and the pressure at the time of zero flow volume as the second index value, and calculate the first pressure ratio, which is the ratio of the first index value to the second index value.

5. The medical-information processing apparatus according to claim 1, wherein the processing circuitry is configured to use at least any one of a blood pressure of a right atrium and zero as the pressure lower than the pressure at the time of zero flow volume to calculate, as the second pressure ratio, at least any one of a ratio of a pressure based on the pressure on the upstream side and the pressure of the right atrium to a pressure based on the pressure on the downstream side and the pressure of the right atrium and a ratio of the pressure on the upstream side to the pressure on the downstream side.

6. The medical-information processing apparatus according to claim 1, wherein the processing circuitry is configured to present alarm information on the display in accordance with a value of the first pressure ratio and a value of the second pressure ratio.

7. The medical-information processing apparatus according to claim 6, wherein the processing circuitry is configured to present the alarm information on the display in a case where a difference between the value of the first pressure ratio and the value of the second pressure ratio exceeds a predetermined threshold.

8. The medical-information processing apparatus according to claim 6, wherein the processing circuitry is configured to present the alarm information on the display in a case where at least any one of the value of the first pressure ratio and the value of the second pressure ratio is equal to or less than a predetermined threshold.

9. The medical-information processing apparatus according to claim 1, wherein the processing circuitry is configured to generate a graph that indicates a relationship between the volume of blood flow and the pressure in the blood vessel in accordance with an analysis result of the fluid analysis, and present the graph on the display.

10. The medical-information processing apparatus according to claim 9, wherein the processing circuitry is configured to calculate a tilt of the graph, and present a value that indicates the tilt on the display.

11. The medical-information processing apparatus according to claim 9, wherein the processing circuitry is configured to present information that corresponds to a time phase of image data, used for the fluid analysis, on the graph.

12. The medical-information processing apparatus according to claim 1, wherein a time phase where the relationship between the volume of blood flow and the pressure in the blood vessel indicates a proportional relationship is a heart phase 70% to 99%.

13. An X-ray CT apparatus comprising processing circuitry configured to acquire medical image data including a medical image obtained by conducting imaging on a subject in a resting state in a time phase where a relationship between a volume of blood flow and a pressure in a blood vessel in a cardiac cycle of the subject indicates a proportional relationship, extract a structure of the blood vessel of the subject, included in the medical image data, obtain, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel, calculate a first pressure ratio that is a ratio of the first index value to the second index value, and a second pressure ratio that is a ratio of the third index value to the fourth index value, and present the first pressure ratio and the second pressure ratio on a display.

14. A medical-information processing apparatus comprising processing circuitry configured to acquire medical image data including a medical image that is obtained during imaging on a subject in a state where a relationship between a volume of blood flow and a pressure in a blood vessel in a cardiac cycle of the subject is already known, extract a structure of the blood vessel of the subject, included in the medical image data, obtain, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel, calculate a first pressure ratio that is a ratio of the first index value to the second index value, and a second pressure ratio that is a ratio of the third index value to the fourth index value, and present the first pressure ratio and the second pressure ratio on a display.

15. An X-ray CT apparatus comprising processing circuitry configured to acquire medical image data including a medical image obtained by conducting imaging on a subject in a state where a relationship between a volume of blood flow and a pressure in a blood vessel in a cardiac cycle of the subject is already known, extract a structure of the blood vessel of the subject, included in the medical image data, obtain, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel, calculate a first pressure ratio that is a ratio of the first index value to the second index value, and a second pressure ratio that is a ratio of the third index value to the fourth index value, and present the first pressure ratio and the second pressure ratio on a display.

16. A medical-information processing method performed by a medical-information processing apparatus, the medical-information processing method comprising:

acquiring medical image data including a medical image that is obtained during imaging on a subject in a resting state in a time phase where a relationship between a volume of blood flow and a pressure in a blood vessel in a cardiac cycle of the subject indicates a proportional relationship, extracting a structure of the blood vessel of the subject, included in the medical image data, obtaining, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel, calculating a first pressure ratio that is a ratio of the first index value to the second index value, and a second pressure ratio that is a ratio of the third index value to the fourth index value, and presenting the first pressure ratio and the second pressure ratio on a display.

17. The medical-information processing method according to claim 16, wherein calculating the pressures in the blood vessel on the upstream side and on the downstream side and the pressure at the time of zero flow volume.

18. The medical-information processing method according to claim 16, wherein obtaining the second index value and the first pressure ratio with regard to each of positions on the downstream side, and presenting, on the display, the first pressure ratio at each of the positions on the downstream side together with the medical image data in a manner of being related to a corresponding position in the medical image data.

19. The medical-information processing method according to claim 16, wherein obtaining a difference between the pressure in the blood vessel on the upstream side of the predetermined position within the blood vessel and the pressure at the time of zero flow volume as the first index value, obtaining a difference between the pressure in the blood vessel on the downstream side of the predetermined position within the blood vessel and the pressure at the time of zero flow volume as the second index value, and calculating the first pressure ratio, which is the ratio of the first index value to the second index value.

20. The medical-information processing method according to claim 16, wherein using at least any one of a blood pressure of a right atrium and zero as the pressure lower than the pressure at the time of zero flow volume to calculate, as the second pressure ratio, at least any one of a ratio of a pressure based on the pressure on the upstream side and the pressure of the right atrium to a pressure based on the pressure on the downstream side and the pressure of the right atrium and a ratio of the pressure on the upstream side to the pressure on the downstream side.

21. The medical-information processing method according to claim 16, wherein presenting alarm information on the display in accordance with a value of the first pressure ratio and a value of the second pressure ratio.

22. The medical-information processing method according to claim 20, wherein presenting the alarm information on the display in a case where a difference between the value of the first pressure ratio and the value of the second pressure ratio exceeds a predetermined threshold.

23. The medical-information processing method according to claim 21, wherein presenting the alarm information on the display in a case where at least any one of the value of the first pressure ratio and the value of the second pressure ratio is equal to or less than a predetermined threshold.

24. The medical-information processing method according to claim 16, wherein
generating a graph that indicates a relationship between the volume of blood flow and the pressure in the blood vessel in accordance with an analysis result of the fluid analysis, and
presenting the graph on the display.

25. The medical-information processing method according to claim 24, wherein
calculating a tilt of the graph, and
presenting a value that indicates the tilt on the display.

26. The medical-information processing method according to claim 24, wherein presenting information that corresponds to a time phase of image data, used for the fluid analysis, on the graph.

27. The medical-information processing method according to claim 16, wherein a time phase where the relationship between the volume of blood flow and the pressure in the blood vessel indicates a proportional relationship is a heart phase 70% to 99%.

28. A medical-information processing system comprising processing circuitry configured to
acquire medical image data including a medical image that is obtained during imaging on a subject in a resting state in a time phase where a relationship between a volume of blood flow and a pressure in a blood vessel in a cardiac cycle of the subject indicates a proportional relationship,
extract a structure of the blood vessel of the subject, included in the medical image data,
obtain, in accordance with a relation between a volume of blood flow and a pressure in the blood vessel, a first index value, which is obtained based on a pressure in the blood vessel on an upstream side of a predetermined position within the blood vessel and a pressure at a time of zero flow volume, which indicates a pressure in the blood vessel in a case where the volume of blood flow within the blood vessel is zero, a second index value, which is obtained based on a pressure in the blood vessel on a downstream side of the predetermined position and the pressure at the time of zero flow volume, a third index value, which is obtained based on the pressure in the blood vessel on the upstream side of the predetermined position within the blood vessel and a pressure, which is lower than the pressure at the time of zero flow volume, and a fourth index value, which is obtained based on the pressure in the blood vessel on the downstream side of the predetermined position and the pressure, which is lower than the pressure at the time of zero flow volume, by applying fluid analysis to the structure of the blood vessel,
calculate a first pressure ratio that is a ratio of the first index value to the second index value, and a second pressure ratio that is a ratio of the third index value to the fourth index value, and
present the first pressure ratio and the second pressure ratio on a display.

29. The medical-information processing system according to claim 28, wherein the processing circuitry is configured to calculate the pressures in the blood vessel on the upstream side and on the downstream side and the pressure at the time of zero flow volume.

30. The medical-information processing system according to claim 28, wherein the processing circuitry is configured to
obtain the second index value and the first pressure ratio with regard to each of positions on the downstream side, and
present, on the display, the first pressure ratio at each of the positions on the downstream side together with the medical image data in a manner of being related to a corresponding position in the medical image data.

31. The medical-information processing system according to claim 28, wherein the processing circuitry is configured to
obtain a difference between the pressure in the blood vessel on the upstream side of the predetermined position within the blood vessel and the pressure at the time of zero flow volume as the first index value,
obtain a difference between the pressure in the blood vessel on the downstream side of the predetermined position within the blood vessel and the pressure at the time of zero flow volume as the second index value, and
calculate the first pressure ratio, which is the ratio of the first index value to the second index value.

32. The medical-information processing system according to claim 28, wherein the processing circuitry is configured to use at least any one of a blood pressure of a right atrium and zero as the pressure lower than the pressure at the time of zero flow volume to calculate, as the second pressure ratio, at least any one of a ratio of a pressure based on the pressure on the upstream side and the pressure of the right atrium to a pressure based on the pressure on the downstream side and the pressure of the right atrium and a ratio of the pressure on the upstream side to the pressure on the downstream side.

33. The medical-information processing system according to claim 28, wherein the processing circuitry is configured to present alarm information on the display in accordance with a value of the first pressure ratio and a value of the second pressure ratio.

34. The medical-information processing system according to claim 33, wherein the processing circuitry is configured to present the alarm information on the display in a case where a difference between the value of the first pressure ratio and the value of the second pressure ratio exceeds a predetermined threshold.

35. The medical-information processing system according to claim 33, wherein the processing circuitry is configured to present the alarm information on the display in a case where at least any one of the value of the first pressure ratio and the value of the second pressure ratio is equal to or less than a predetermined threshold.

36. The medical-information processing system according to claim 28, wherein the processing circuitry is configured to
generate a graph that indicates a relationship between the volume of blood flow and the pressure in the blood vessel in accordance with an analysis result of the fluid analysis, and
present the graph on the display.

37. The medical-information processing system according to claim 36, wherein the processing circuitry is configured to
calculate a tilt of the graph, and
present a value that indicates the tilt on the display.

38. The medical-information processing system according to claim 36, wherein the processing circuitry is configured to present information that corresponds to a time phase of image data, used for the fluid analysis, on the graph.

39. The medical-information processing system according to claim 28, wherein a time phase where the relationship between the volume of blood flow and the pressure in the blood vessel indicates a proportional relationship is a heart phase 70% to 99%.

* * * * *